(12) United States Patent
Lui et al.

(10) Patent No.: US 10,906,976 B2
(45) Date of Patent: Feb. 2, 2021

(54) INDUCTION OF IMMUNOTOLERANCE TO IMPROVE ACCEPTANCE OF TISSUE DERIVED FROM PLURIPOTENT STEM CELLS

(71) Applicant: The Chinese University of Hong Kong, Hong Kong (CN)

(72) Inventors: Oi Lan Kathy Lui, Hong Kong (CN); Herman Waldmann, Oxford (GB)

(73) Assignee: The Chinese University of Hong Kong, Hong Kong (CN)

( * ) Notice: Subject to any disclaimer, the term of this patent is extended or adjusted under 35 U.S.C. 154(b) by 556 days.

(21) Appl. No.: 15/360,347

(22) Filed: Nov. 23, 2016

(65) Prior Publication Data
US 2017/0151327 A1    Jun. 1, 2017

Related U.S. Application Data

(60) Provisional application No. 62/261,632, filed on Dec. 1, 2015.

(51) Int. Cl.
*C07K 16/28* (2006.01)
*A61K 35/12* (2015.01)
*A61K 39/00* (2006.01)

(52) U.S. Cl.
CPC .......... *C07K 16/2815* (2013.01); *A61K 35/12* (2013.01); *C07K 16/2812* (2013.01); *C07K 16/2875* (2013.01); *A61K 2039/505* (2013.01); *A61K 2039/507* (2013.01); *C07K 2317/75* (2013.01); *C07K 2317/76* (2013.01)

(58) Field of Classification Search
None
See application file for complete search history.

(56) References Cited

U.S. PATENT DOCUMENTS

2011/0064705 A1 *    3/2011    Lanza ................. C12N 5/0647
424/93.7

FOREIGN PATENT DOCUMENTS

WO    WO-2010023482 A2 *    3/2010    ......... C07K 16/2815

OTHER PUBLICATIONS

Graca et al. (BMC Immunology 2006, 7:9) (Year: 2006).*
phenotype information for CBA/J, Jackson Laboratories, Sep. 10, 2015, pp. 1-5 (Year: 2015).*
Nikolik et al., Transplantation 2010;89: 23-32. (Year: 2010).*
Waldmann et al., Clin Invest. 2014;124(4):1439-1445. (Year: 2014).*
Liu et al. (Nat Commun. Dec. 1, 2014;5:5629). (Year: 2014).*
FDA, "Guidance for Industry Estimating the Maximum Safe Starting Dose in Initial Clinical Trials for Therapeutics in Adult Healthy Volunteers," 2005, pp. 1-27. (Year: 2005).*

* cited by examiner

*Primary Examiner* — Zachary S Skelding
(74) *Attorney, Agent, or Firm* — Kilpatrick Townsend & Stockton LLP

(57) ABSTRACT

The present invention provides for a novel method for inhibiting an undesirable immune response, especially in transplant recipients such as those having received an allogeneic stem cell transplant. Also disclosed are related compositions and kits for inducing immunotolerance.

16 Claims, 13 Drawing Sheets
Specification includes a Sequence Listing.

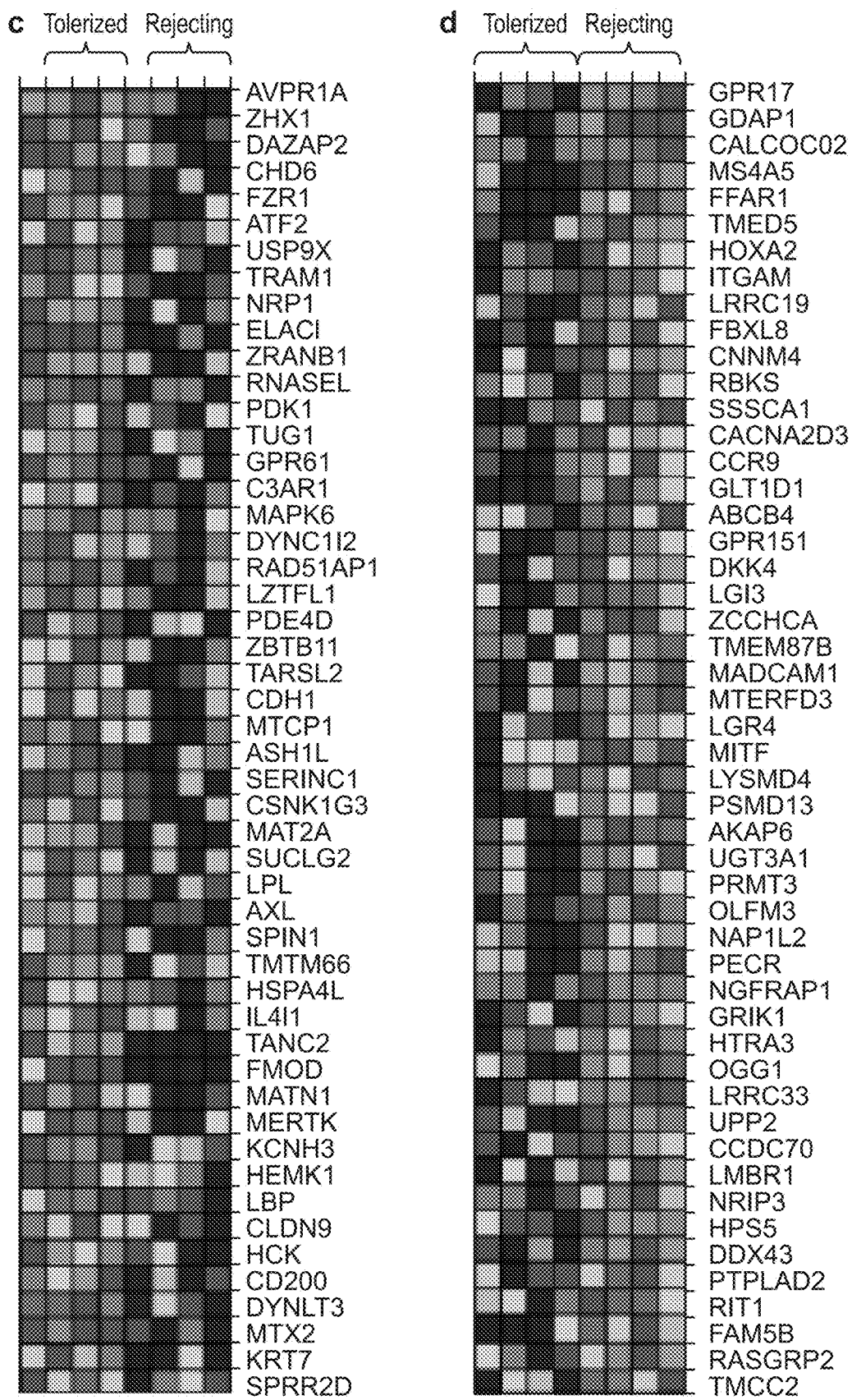
FIG. 5 (Cont. 1)

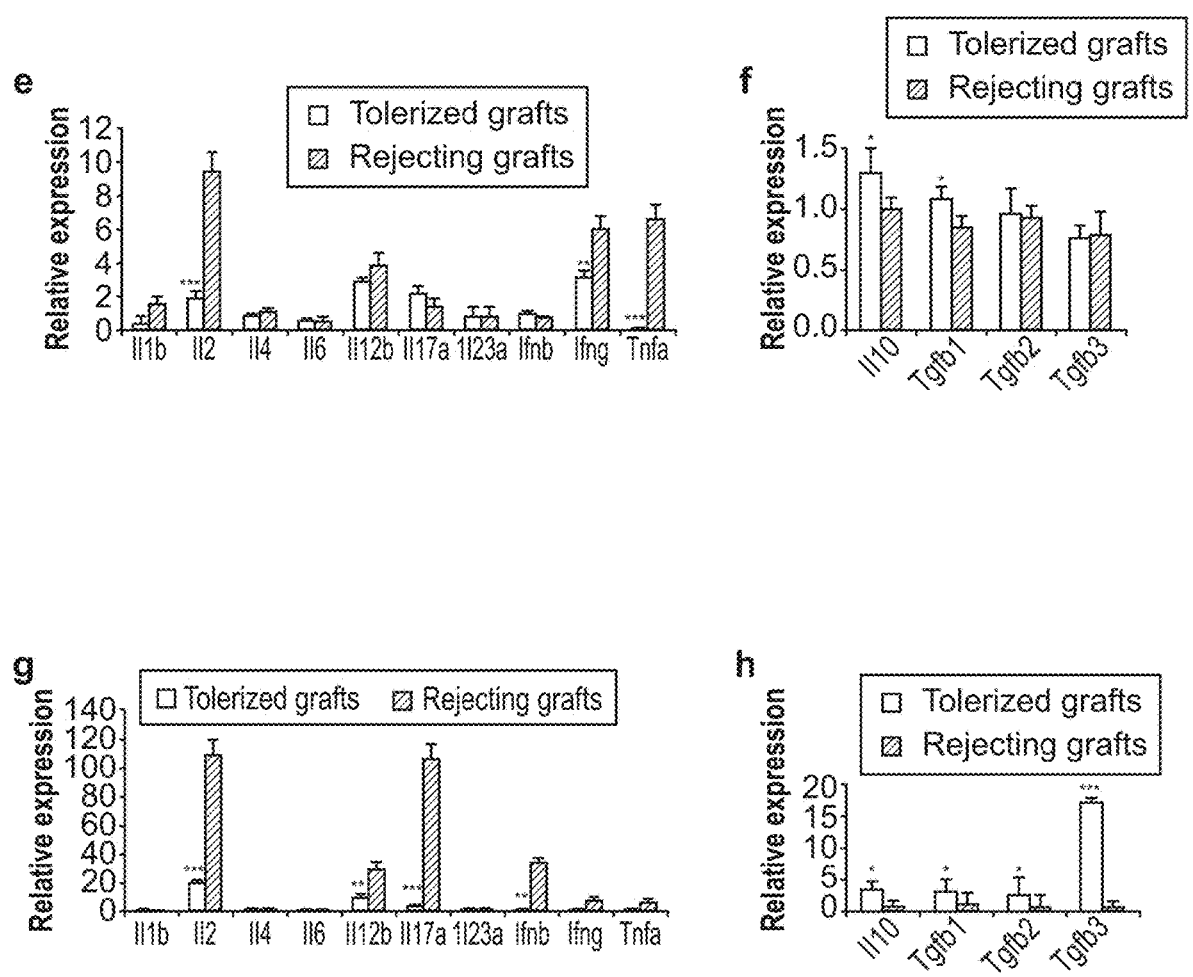
FIG. 5 (Cont. 2)

SEQUENCE LISTING

<160> NUMBER OF SEQ ID NOS: 72

<210> SEQ ID NO 1
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 1
aacagtgttg acatgaagag cc                                      22

<210> SEQ ID NO 2
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 2
tgatggcgaa gcgagtgaag                                         20

<210> SEQ ID NO 3
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 3
agagtggagc ctggtcttac a                                       21

<210> SEQ ID NO 4
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 4
ggagcgagat ccctccaaaa t                                       21

<210> SEQ ID NO 5
<211> LENGTH: 19
<212> TYPE: DNA
<213> ORGANISM: Artificial Sequence
<220> FEATURE:
<223> OTHER INFORMATION: synthetic qPCR primer sequence

<400> SEQUENCE: 5
ctgcggctcg atcaactca                                          19

<210> SEQ ID NO 6
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 6
atgcccagac atctgtgtcc                                         20

<210> SEQ ID NO 7
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 7
ctgctctacg acatgaacgg                                         20

<210> SEQ ID NO 8
<211> LENGTH: 23
<212> TYPE: DNA
<213> ORGANISM: Artificial Sequence

```
<220> FEATURE:
<223> OTHER INFORMATION: synthetic qPCR primer sequence

<400> SEQUENCE: 8
gcggagtgta atcagtattt gga                                             23

<210> SEQ ID NO 9
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 9
ggcccaataa tcagagtggc a                                               21

<210> SEQ ID NO 10
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 10
gtccctgagc agatttagct g                                               21

<210> SEQ ID NO 11
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 11
tcaggcgtct gtagaggctt                                                 20

<210> SEQ ID NO 12
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 12
ctgctaccct tgagacacct g                                               21

<210> SEQ ID NO 13
<211> LENGTH: 19
<212> TYPE: DNA
<213> ORGANISM: Artificial Sequence
<220> FEATURE:
<223> OTHER INFORMATION: synthetic qPCR primer sequence

<400> SEQUENCE: 13
ccaagcggct acacgtctc                                                  19

<210> SEQ ID NO 14
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 14
atgaccaaat cgtacagcga g                                               21
```

```
<210> SEQ ID NO 15
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 15
tactatgcgg tttcccaggc                                               20

<210> SEQ ID NO 16
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 16
ccagagcccg atgaccttt t                                              21

<210> SEQ ID NO 17
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 17
actgccagaa tcgctacaca g                                             21

<210> SEQ ID NO 18
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 18
tggccctcat cgacgttttc                                               20

<210> SEQ ID NO 19
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 19
ttagccagct tagttctctg tgg                                           23

<210> SEQ ID NO 20
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 20
gggaagatgg tcgtgatcct t                                             21

<210> SEQ ID NO 21
<211> LENGTH: 19
<212> TYPE: DNA
<213> ORGANISM: Artificial Sequence
<220> FEATURE:
<223> OTHER INFORMATION: synthetic qPCR primer sequence
```

```
<400> SEQUENCE: 21
ccgatgcagc cttttcgga                                              19

<210> SEQ ID NO 22
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 22
tgtaaaacag cacgtcatcc tt                                          22

<210> SEQ ID NO 23
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 23
actcatccat acacaggacc c                                           21

<210> SEQ ID NO 24
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 24
cctttgctga caataagcac tgg                                         23

<210> SEQ ID NO 25
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 25
ggctgttgtc atacttctca tgg                                         23

<210> SEQ ID NO 26
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 26
tccagcgact caatcttcct c                                           21

<210> SEQ ID NO 27
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 27
ggggtctcta tgcccaacaa                                             20

<210> SEQ ID NO 28
```

```
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 28
gaaggtccct gatgtagtcg at                                              22

<210> SEQ ID NO 29
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 29
gcatttgatc ccgtacaacc t                                               21

<210> SEQ ID NO 30
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 30
ccagtgtcat ttccgatcac ttt                                             23

<210> SEQ ID NO 31
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 31
gaatcccttg tgagccgatt t                                               21

<210> SEQ ID NO 32
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 32
atgcacatcc ttcgataaga ctg                                             23

<210> SEQ ID NO 33
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 33
gggctctgat ctctgcatct ac                                              22

<210> SEQ ID NO 34
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 34
```
cgtcccattc agcttctccc                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 35
gttcatggct tcgaggtcgt                                               20

<210> SEQ ID NO 36
<211> LENGTH: 19
<212> TYPE: DNA
<213> ORGANISM: Artificial Sequence
<220> FEATURE:
<223> OTHER INFORMATION: synthetic qPCR primer sequence

<400> SEQUENCE: 36
gctgagtagg gcaggatga                                                19

<210> SEQ ID NO 37
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 37
cactgcctcc tagcttgtcc                                               20

<210> SEQ ID NO 38
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 38
cacccatgtc catgtcttat tgt                                           23

<210> SEQ ID NO 39
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 39
atgttcaaag aactcgtggc a                                             21

<210> SEQ ID NO 40
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 40
agcatcagat acaagaggta ggg                                           23

<210> SEQ ID NO 41
<211> LENGTH: 21
<212> TYPE: DNA

```
<213> ORGANISM: Artificial Sequence
<220> FEATURE:
<223> OTHER INFORMATION: synthetic qPCR primer sequence

<400> SEQUENCE: 41
tctggggtgg tctcgatttt a                                          21

<210> SEQ ID NO 42
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 42
tccccaagat acacggagag g                                          21

<210> SEQ ID NO 43
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 43
aggtcggtgt gaacggattt g                                          21

<210> SEQ ID NO 44
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 44
atgaccaaca agtgtctcct cc                                         22

<210> SEQ ID NO 45
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 45
atgaacgcta cacactgcat c                                          21

<210> SEQ ID NO 46
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 46
gcaactgttc ctgaactcaa ct                                         22

<210> SEQ ID NO 47
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 47
tgagcaggat ggagaattac agg                                        23
```

<210> SEQ ID NO 48
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 48
ggtctcaacc cccagctagt                                              20

<210> SEQ ID NO 49
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 49
tagtccttcc taccccaatt tcc                                          23

<210> SEQ ID NO 50
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 50
gctcttactg actggcatga g                                            21

<210> SEQ ID NO 51
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 51
tggtttgcca tcgttttgct g                                            21

<210> SEQ ID NO 52
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 52
tttaactccc ttggcgcaaa a                                            21

<210> SEQ ID NO 53
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 53
atgctggatt gcagagcagt a                                            21

<210> SEQ ID NO 54
<211> LENGTH: 19
<212> TYPE: DNA
<213> ORGANISM: Artificial Sequence
<220> FEATURE:

<223> OTHER INFORMATION: synthetic qPCR primer sequence

<400> SEQUENCE: 54
ggccagatcc tgtccaagc                                              19

<210> SEQ ID NO 55
<211> LENGTH: 19
<212> TYPE: DNA
<213> ORGANISM: Artificial Sequence
<220> FEATURE:
<223> OTHER INFORMATION: synthetic qPCR primer sequence

<400> SEQUENCE: 55
cttcgacgtg acagacgct                                              19

<210> SEQ ID NO 56
<211> LENGTH: 19
<212> TYPE: DNA
<213> ORGANISM: Artificial Sequence
<220> FEATURE:
<223> OTHER INFORMATION: synthetic qPCR primer sequence

<400> SEQUENCE: 56
cctggccctg ctgaacttg                                              19

<210> SEQ ID NO 57
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 57
cctctctcta atcagccctc tg                                          22

<210> SEQ ID NO 58
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 58
tgtagaccat gtagttgagg tca                                         23

<210> SEQ ID NO 59
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 59
ggaatccaag caagttgtag ctc                                         23

<210> SEQ ID NO 60
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 60
ccatcctttt gccagttcct c                                           21

<210> SEQ ID NO 61
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 61
atcttttggg gtccgtcaac t                                        21

<210> SEQ ID NO 62
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 62
gtccaagttc atcttctagg cac                                      23

<210> SEQ ID NO 63
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 63
gccgatgatc tctctcaagt gat                                      23

<210> SEQ ID NO 64
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 64
ttggtcctta gccactcctt c                                        21

<210> SEQ ID NO 65
<211> LENGTH: 20
<212> TYPE: DNA
<213> ORGANISM: Artificial Sequence
<220> FEATURE:
<223> OTHER INFORMATION: synthetic qPCR primer sequence

<400> SEQUENCE: 65
cgcagctcta ggagcatgtg                                          20

<210> SEQ ID NO 66
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 66
acaggtgagg ttcactgttt ct                                       22

<210> SEQ ID NO 67
<211> LENGTH: 20
<212> TYPE: DNA
<213> ORGANISM: Artificial Sequence
<220> FEATURE:
<223> OTHER INFORMATION: synthetic qPCR primer sequence

```
<400> SEQUENCE: 67
ctttccctcc gcattgacac                                              20

<210> SEQ ID NO 68
<211> LENGTH: 23
<212> TYPE: DNA
<213> ORGANISM: Artificial Sequence
<220> FEATURE:
<223> OTHER INFORMATION: synthetic qPCR primer sequence

<400> SEQUENCE: 68
acggggcaca ttatttttag tct                                          23

<210> SEQ ID NO 69
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 69
gtgggtttcc accattagca c                                            21

<210> SEQ ID NO 70
<211> LENGTH: 22
<212> TYPE: DNA
<213> ORGANISM: Artificial Sequence
<220> FEATURE:
<223> OTHER INFORMATION: synthetic qPCR primer sequence

<400> SEQUENCE: 70 gcagggcag tgtaaactta tt                                            22

<210> SEQ ID NO 71
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 71
ttgatgtggc cgaagtccaa c                                            21

<210> SEQ ID NO 72
<211> LENGTH: 21
<212> TYPE: DNA
<213> ORGANISM: Artificial Sequence
<220> FEATURE:
<223> OTHER INFORMATION: synthetic qPCR primer sequence

<400> SEQUENCE: 72
gaggacctgg gagtagatga g                                            21
```

INDUCTION OF IMMUNOTOLERANCE TO IMPROVE ACCEPTANCE OF TISSUE DERIVED FROM PLURIPOTENT STEM CELLS

RELATED APPLICATIONS

This application claims priority to U.S. Provisional Patent Application No. 62/261,632, filed Dec. 1, 2015, the contents of which are incorporated by reference in the entirety for all purposes.

BACKGROUND OF THE INVENTION

There is increasing interest in transplantation of human stem cells for therapeutic purposes. It will provide great benefits to future applications if the cells' long-term acceptance and functional differentiation in allogeneic hosts can be achieved with minimal immunosuppression. Allogeneic stem cell transplants differ from conventional tissue transplants insofar as not all alloantigens are revealed during tolerance induction. This risks that the immune system tolerized to antigens expressed by progenitors may still remain responsive to antigens expressed later during differentiation. Here the inventors show that brief induction with monoclonal antibody-mediated coreceptor and costimulation blockade enables long-term engraftment and tolerance towards murine embryonic stem cells (ESCs), hESCs, human induced pluripotent stem cells (iPSCs) and hESC-derived progenitors in outbred murine recipients. Tolerance induced to PSC-derived progenitors extends to their differentiated progenies, and sometimes even to different tissues derived from the same donor. Global gene expression profiling identifies clear features in T cells from tolerized grafts that are distinct from those involved in rejection.

BRIEF SUMMARY OF THE INVENTION

This invention provides novel methods and compositions useful for inhibiting undesirable immune response in patients receiving allogenic transplantation such as stem cell transplantation. This invention thus provides valuable tool for preventing immune rejection, such as ensuring engraftment and survival of human pluripotent stem cell derivatives after transplantation into immunocompetent individuals, permitting safe and effective use of human stem cells including pluripotent stem cell derivatives in therapeutic contexts. By administration of antibodies against CD4, CD8 and optionally CD40 ligand (CD40L) immediately before or after transplantation procedure (e.g., on days −7, −6, −5, −4, −3, −2, −1, 0, 1, 2, 3, 4, 5, 6 and 7 in relation to transplantation taking place on day 0, with "−" denoting days prior to and "+" denoting days after transplantation), the present inventors have demonstrated a simple protocol to induce long-term immunotolerance with a short course of coreceptor and costimulation blockade. Specifically, while previously used methods focus on costimulation blockade only, the present inventors discovered that blockade of both costimulation and coreceptor is exceptionally effective as demonstrated in: (a) long-term survival of the tolerized grafts persists for at least six months even after washout of the coreceptor and costimulation blocking antibodies three months post transplantation; (b) tolerance was maintained in an antigen-specific manner and the recipient's immune system retains its ability to reject third-party antigens; (c) tolerance protects second grafts that express a common set of antigens through linked suppression; and (d) regulatory T cells were involved in the process against immune rejection.

Thus, in the first aspect, the present invention provides a composition comprising an effective amount of an antibody against CD4 and an antibody against CD8, optionally further comprising an effective amount of an antibody against CD40L, for the purpose of inducing immunotolerance in a recipient's body or for inhibiting an immune response in a subject. The composition often comprises a physiologically acceptable excipient, in addition to the antibodies. In some cases, the composition is formulated for injection, such as intraperitoneal injection as well as intravenous, intramuscular, or subcutaneous injection. In some cases, the composition is formulated in a dosed form, each containing an effective amount of each of the antibodies for one administration (e.g., one injection). Optionally, one or more immune suppressants are included in the composition.

In a second aspect, the present invention provides a method for suppressing an undesirable immune response or inducing immunotolerance in a subject. The method comprises the step of administering to the subject an effective amount of an antibody against CD4 and an effective amount of an antibody against CD8, such as by administering one of the compositions described above.

In some embodiments, this method also includes administering to the subject an effective amount of an antibody against CD40L. In some embodiments, all antibodies are administered together at the same time, for example, they may be administered all together in a single composition, such as those described above and herein. In some embodiments, the antibodies are administered by injection, for instance, intraperitoneally, intravenously, intramuscularly, or subcutaneously. In some embodiments, the subject is a patient (e.g., a human patient) who is about to receive or has just received a transplant procedure, such as a stem cell transplant. This method is typically practiced within 7 days before or after the transplant procedure but may take places within 14 days before or after the procedure. For human therapeutic uses, at least one or more, preferable all, of the antibodies being administered are humanized antibodies, especially humanized monoclonal antibodies. In some embodiments, the administering step is performed once, twice, three times or four times in total, preferably once per day on days 0-6 post transplantation or once every other day on days 0-6 post transplantation. In some embodiments, about 1-1000 mg, about 10-100 mg, about 20-50 mg, about 30, 40, or 50 mg of each antibody is administered each time to the subject per kg of the subject's body weight. As the immune tolerance-inducing method of this invention general enjoys a very high level of efficacy, no additional means of suppression of a transplant receipt's immune system is necessary. Thus, this method is typically practiced without the co-administration of any known immune suppressant during the same time period when the antibodies are given the patient, although it remains an option that one or more immune suppressants could be co-administered in order to achieve an enhanced effect.

In a third aspect, the present invention provides a kit for suppressing an undesirable immune response or for inducing immunotolerance in a subject, such as a patient (e.g., a human patient) who is about to receive or has just received a transplant procedure (e.g., a stem cell transplant. The components, an antibody against CD4 and an antibody against CD8, optionally with an antibody against CD40L, may be placed together (two or more antibodies) in the same container or may be placed in separate containers, each container contains one or two antibodies.

In some embodiments, the kit includes a first container containing an antibody against CD4 and a second container containing an antibody against CD8, optionally with a third container containing an antibody against CD40L. In some embodiments, the kit includes a first container containing an antibody against CD4 and an antibody against CD8, and a second container containing an antibody against CD40L. In some embodiments, the kit includes a first container containing an antibody against CD4 and an antibody against CD40L, and a second container containing an antibody against CD8. In some embodiments, the kit includes a first container containing an antibody against CD8 and an antibody against CD40L, a second container containing an antibody against CD4. In some embodiments, the kit includes a container containing an antibody against CD4, a container containing an antibody against CD8, and an antibody against CD40L. Of all these possible arrangements, each container in the kit may contain a composition comprising one or more antibodies plus at least one a physiologically acceptable excipient. In some cases, and the composition is formulated for injection and containing an effective amount of each antibody for one injection. The kit usually contains instructional material describing the proper usage of the kit such as dosing and administration schedule. As a further option, one or more immune suppressants may be included in the kit. For human therapeutic uses, at least one or more, preferable all, of the antibodies in the kits described above and herein are humanized antibodies, especially humanized monoclonal antibodies.

indicates cysts formed within teratomas; and an asterisk indicates host kidney. (C-E) Representative H&E images showing tissues of the (C) ectoderm, (D) mesoderm, and (E) endoderm lineages (n=5). Scale bar=100 μM.

Figure 7:
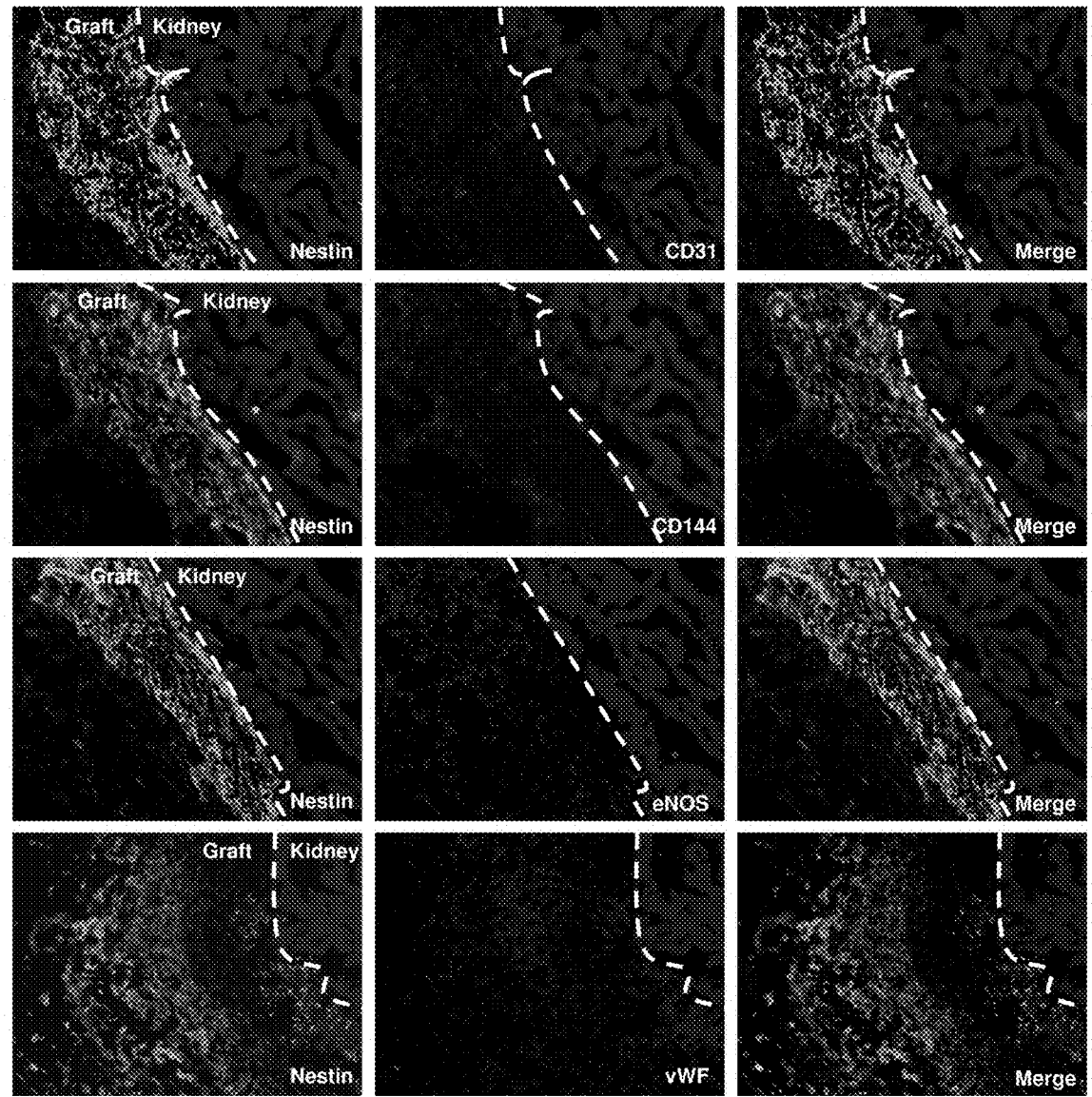

FIG. 7 Neural grafts do not express antigens considered unique to CD31$^+$CD144$^+$ endothelial progenitor cells. Immunostaining of neural cell-specific marker, Nestin (green) and endothelial cell-specific markers, CD31, CD144, eNOS or vWF (red) by neural grafts transplanted 30 days under the kidney capsules. Sections were chosen for immunostaining with alternative slides of the same recipient or of different recipients.

Figure 8:
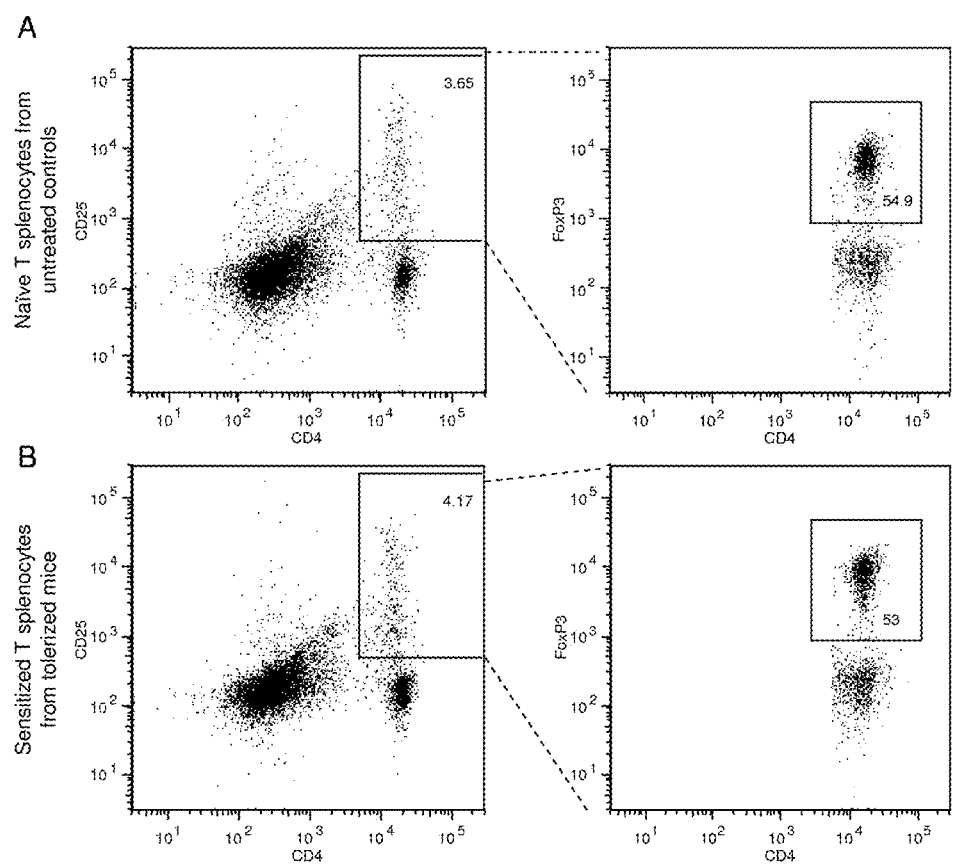

FIG. 8 Proportion of splenic CD4$^+$FoxP3$^+$ cells in tolerized and naïve mice. Splenic CD4$^+$FoxP3$^+$ cells were isolated from (A) untreated mice and (B) anti-CD4, -CD8 and -CD40L mAbs-treated recipients following transplantation of hESC-derived neural progenitor cells for 30 days.

Figure 9:
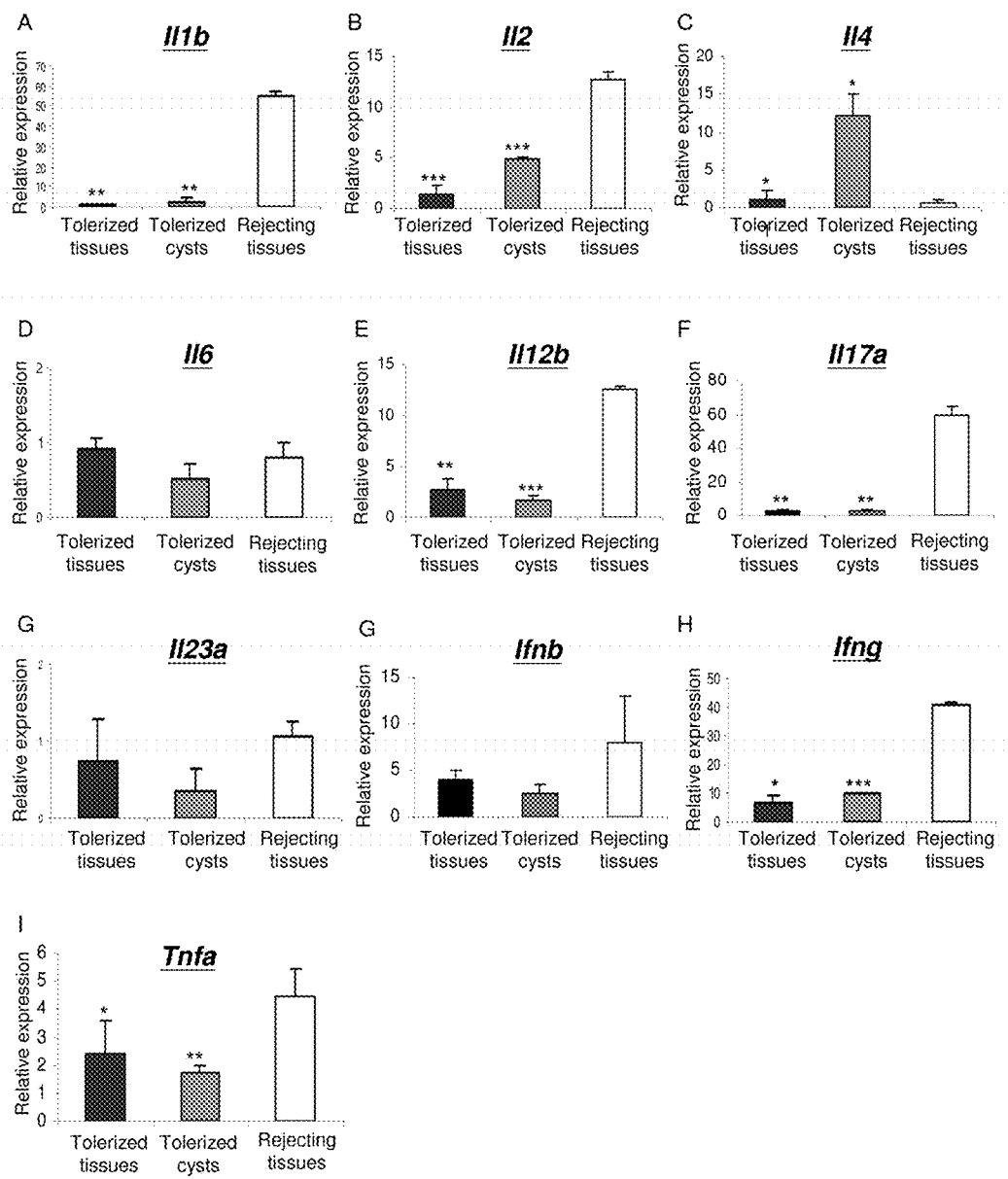

FIG. 9 Tolerized EB grafts express less pro-inflammatory cytokine genes compared to that of rejecting EB grafts. (3 months post transplantation) (A-I) Quantitative RT-PCR of hESC-derived teratomas isolated from untreated recipients (rejecting grafts) or anti-CD4, -CD8 and -CD40L mAbs-treated recipients (tolerized tissues or cysts) on day 90 of transplantation; expression levels of the pro-inflammatory cytokines were compared to that of undifferentiated hESCs (value on y-axis=1).

Figure 10:
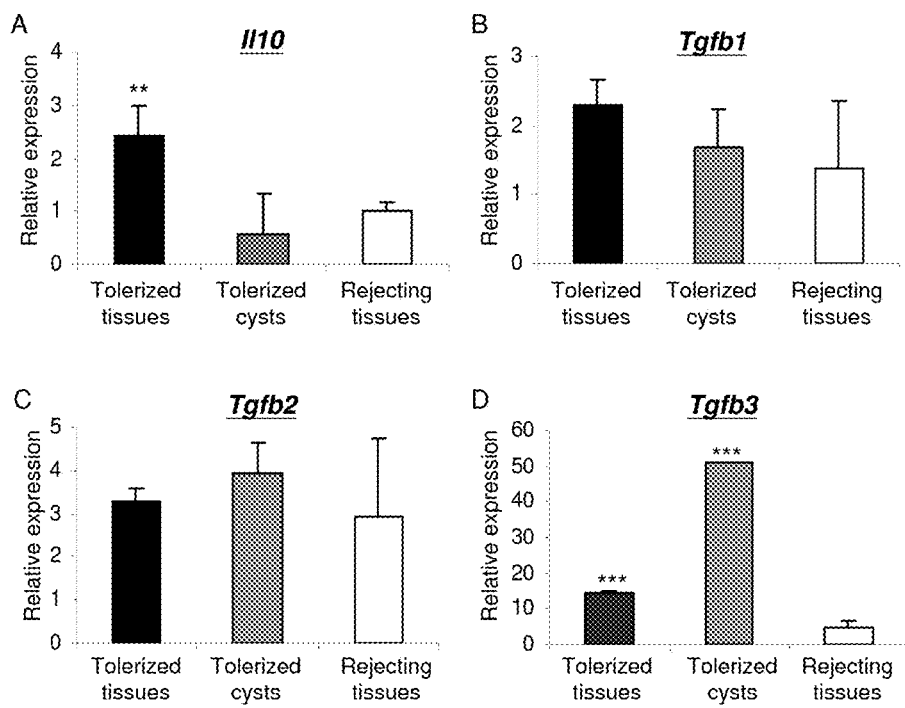

FIG. 10 Tolerized EB grafts express more anti-inflammatory cytokine genes compared to that the rejecting EB grafts. (3 months post transplantation) (A-D) Quantitative RT-PCR of hESC-derived teratomas isolated from untreated recipients (rejecting grafts) or anti-CD4, -CD8 and -CD40L mAbs-treated recipients (tolerized tissues or cysts) on day 90 of transplantation; expression levels of the anti-inflammatory cytokines were compared to that of undifferentiated hESCs (value on y-axis=1).

DEFINITIONS

The term "inhibiting" or "inhibition," as used herein, refers to any detectable negative effect on a target biological process, such as an immune response observed in a transplant recipient, which may lead to the rejection of transplanted cells, tissue, or organ. Typically, an inhibition of immunorejection is reflected in a decrease of at least 10%, 20%, 30%, 40%, 50%, 60%, 70%, 80%, 90% or higher, including 100% or complete elimination, of the instances or percentage of post-transplant rejection, when compared to a control not given the "inhibition" treatment, such as treatment by administration of antibodies described herein. On the other hand, inhibition of an undesirable immune response such as rejection in a transplant recipient may also be manifested as induced immunotolerance in the host, demonstrated in an increase of at least 50%, 60%, 70%, 80%, 90%, 100%, 200%, 300%, 500% or more in the time of survival of the transplanted cells, tissue, or organ within the recipient body after the transplant procedure.

The term "CD4 (cluster of differentiation 4)" refers to a glycoprotein found on the surface of various immune cells such as T helper cells, monocytes, macrophages, and dendritic cells. The human CD4 protein and CD4 gene are described in Isobel et al. (*Proc. Natl. Acad. Sci. U.S.A.* 83(12): 4399-4402, 1986) and Ansari-Lari et al. (*Genome Res.* 6(4): 314-326, 1996).

The term "CD8" refers to a transmembrane glycoprotein that serves as a co-receptor for the T cell receptor (TCR). Like the TCR, CD8 binds to a major histocompatibility complex (MHC) molecule, but CD8 is specific for the class I MHC protein. There are two isoforms of the protein, alpha and beta, each encoded by a different gene. In humans, both genes are located on chromosome 2 in position 2p12, see, e.g., Littman D R: The structure of the CD4 and CD8 genes. *Annu Rev Immunol.* 1987; 5:561-84.

The term "CD40L" or CD40 ligand is also known as CD154, a protein that is primarily expressed on activated T cells and is a member of the tumor necrosis factor (TNF) superfamily. CD40L binds to CD40 on antigen-presenting cells (APC), which may leads to varying effects depending on the target cell type. There are three known binding partners for CD40L: CD40, α5β1 integrin, and αIIbβ3 integrin. CD40L acts as a costimulatory molecule and is of particular importance to a subset of T cells called T follicular helper cells (TFH cells). On TFH cells, CD40L plays an important role in B cell maturation by engaging CD40 on the B cell surface and therefore facilitating cell-cell communication.

The term "about" when used in reference to a given value denotes a range of ±10% of the value.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, the amino acid sequence for a CD4 protein variant has at least 80% identity, preferably 85%, 90%, 91%, 92%, 93, 94%, 95%, 96%, 97%, 98%, 99%, or 100% identity, to a reference sequence, e.g., a wild-type human CD4 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89: 10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces therapeutic effects for which a substance is administered. The effects include the prevention, correction, or inhibition of progression of the symptoms of a disease/condition and related complications to any detectable extent, e.g., an immune response such as a post-transplant rejection reaction. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

As used herein, "allogeneic transplant" refers to a transplant process in which a host receives tissue, organ, or cells from another individual of the same species, for example, one human patient receives organ, tissue, or cells derived from another human acting as a donor.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) Nature 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

DETAILED DESCRIPTION OF THE INVENTION

I. Introduction

The unique capacity of human pluripotent stem cells (PSCs), including the best studied embryonic stem cells (hESCs) and induced PSCs (hiPSCs), to self-renew and terminally differentiate into most cell lineages has catalysed research in tissue regeneration. Indeed, a recent report has documented the first evidence of generation of a three-dimensional, vascularized and functional human liver from hiPSCs[1]. Despite many reports describing protocols to derive a variety of cell types from hiPSCs, issues of immunogenicity remain controversial, even following 'autologous' transplantation[2,3]. Moreover, the prospect for patient-specific cell replacement therapy (CRT) seems unlikely for logistical and commercial reasons. Therefore, hESCs still remain a potentially useful cell source for CRT. Trials have been launched to study the potential therapeutic applications of hESC derived oligodendrocyte progenitor cells[4] and hESC-derived retinal pigment epithelial cells[5] in patients with acute spinal cord injury and Stargardt's macular dystrophy, respectively. Many more such trials are likely to be launched in the next 5-10 years[6].

It was previously demonstrated that ESC-derived tissues may exhibit an inherent degree of immune privilege that can contribute to their acceptance in allogeneic recipients[7,8]. This is, in part, likely due to a paucity of donor antigen-presenting cells capable of directly presenting alloantigens to T cells and absence of donor lymphocytes that can contribute to inflammation by generation of graft-versus-host reactions. In some circumstances, regulatory T cells (Treg) are also recruited or differentiated de novo from naive T cells to suppress rejection[7-9], as seen in transplants of differentiated tissues in conventional organ transplantation. One would like to be able to use short-term therapies to tolerize hosts to avoid the long-term problems to both recipient and transplanted tissue associated with conventional immunosuppression. In the context of stem cell-based CRT, certain of the conventional immunosuppressants such as cyclosporine and dexamethasone can strongly inhibit terminal differentiation of neural progenitor cells into mature neurons[10]. Therefore, the ideal immunosuppressants would be those with least toxicity and least effect on cell maturation and function, yet capable of providing long-term benefit from short-term therapy; in other words, able to induce immunological tolerance.

However, unlike conventional tissue grafts, ESC-derived grafts pose a novel challenge for tolerance-inducing strategies, because cells that differentiate from them will carry sets of antigens distinct from those of the parental progenitor cells. In which case, any tolerance induced to the parental progenitor cells would need to be extended to their differentiated progenies. An attractive regimen to achieve this would be the recruitment of antigen specific Treg that could mediate bystander or linked suppression and operate throughout life by continuous harnessing further regulation through infectious tolerance[11-14], a process by which tolerance is transferred from one cell population to another[14]. Although there are reports of antibody-based protocols using costimulation blockade (anti-CD40L, -LFA-1 and CTLA4Ig) that promote short-term acceptance of hESC-derived tissues in rodent model systems15,16, it is unclear whether long-term acceptance (490 days) can be achieved, and if so, whether this could extend to tolerance of differentiated cell types derived from such stem cells.

On the basis of previous rodent studies by the inventors where antibody mediated dominant and infectious tolerance could be induced to fully allogeneic skin grafts[13], it has been reasoned that combined short-term coreceptor/costimulation blockade might offer a simple route to induce acceptance of hPSC-derived tissues. Here the inventors show that such antibody-mediated induction strategies do indeed allow long-term survival and engraftment of human xenografts in mice, in sites not acknowledged as immunologically privileged (for example, beneath the kidney capsule or within the subcutaneous space). It is also demonstrated that tolerance can be induced in this way to hESC-derived progenitor cells of all three embryonic germ layers, as well as their differentiated progenies. Importantly, tolerance to hESC-derived progenitor cells, although specific to the initial inducing antigens, extended to diverse tissue types derived from the same parental stem cells presumably through regulatory mechanisms directed to common antigens expressed by both progenitor cells and their differentiated progenies that produce collateral benefit towards the differentiation-specific antigens. Evidence of any recruitment of T-cell reprogramming towards tolerance is sought by analysis of global gene expression profiling on isolated T cells. The gene expression profiles of T cells infiltrating tolerized and rejecting grafts were found to be very different, likely reflecting the multiple mechanisms underlying the behaviour of tolerant and rejecting populations.

II. Antibodies

The present invention relates to the use of antibodies against CD4, CD8, and/or CD40L to induce immunotolerance in a host for improved efficacy in transplantation, especially human stem cells transplantation. While the appropriate antibodies, such as various monoclonal antibodies with desired antigen specificity, may be commercially available, they can be readily produced according to methods known and well-practiced in the biomedical research field.

Methods of producing polyclonal and monoclonal antibodies that react specifically with a predetermined antigen such as CD4, CD8, and CD40L are known to those of skill in the art (see, e.g., Coligan, Current Protocols in Immunology (1991); Harlow & Lane, Antibodies, A Laboratory Manual (1988); Goding, Monoclonal Antibodies: Principles and Practice (2d ed. 1986); and Kohler & Milstein, Nature 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a predetermined antigen may be used to produce antibodies specifically reactive with the antigen. For example, recombinant CD4, CD8, or CD40L or an antigenic fragment thereof can be expressed in eukaryotic or prokaryotic cells and purified or isolated for further handling. Recombinant protein is the preferred immunogen for the production of monoclonal or polyclonal antibodies. Alternatively, a synthetic peptide derived from an antigen such as CD4, CD8, or CD40L and conjugated to a carrier protein can be used an immunogen. Naturally occurring protein CD4, CD8, or CD40L may also be used either in pure or impure form. The product is then injected into an animal capable of producing antibodies. Either monoclonal or polyclonal antibodies may be generated, for subsequent use in practice of this invention.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, e.g., Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. For a review of immunological and immunoassay procedures, see *Basic and Clinical Immunology* (Stites & Terr eds., 7th ed. 1991). Moreover, the immunoassays can be performed in any of several configurations, which are reviewed extensively in Enzyme Immunoassay. Typically, polyclonal antisera with a titer of $10^4$ or greater are selected and tested for their cross reactivity against their intended antigen, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

III. Pharmaceutical Compositions and Administration

The present invention also provides pharmaceutical compositions or physiological compostions comprising an effective amount of an antibody against CD4, CD8, or CD40L, such antibody often being a monoclonal antibody. Use of the compositions can be in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal administration. The preferred routes of administering the pharmaceutical compositions are intravenous or intraperitoneal delivery to a transplant recipient (e.g., a human patient who is about to receive or has just received a stem cell transplant procedure) at doses of about 50-50,000 mg, 500-5,000 mg, 100-300 mg, 200, 250, or 280 mg of each antibody for a 70 kg adult human per day or every other day. Some exemplary doses and administration frequencies include 10, 20, 30, 40, 50, 60, 70, 80, 90, or 100 mg/kg patient body weight for each antibody in each administration. While all antibodies are often administered at the same doses and schedule, in some case dosage and schedule for each antibody can vary within the ranges described herein. Typically all antibodies are administered to the patient at the same time either on once per day or per two-day basis. The antibodies may be administered in a single pharmaceutical composition or they may be in multiple separate compositions. Similarly, these antibodies may be administered at the same time, or they may be administered on different days but all in close proximity to each other's administration, e.g., one administered on day 1 and other or others administered on day 2, such that the effects of these antibodies being co-administered are obtained. The appropriate dose may be administered in a single daily/bi-daily (once every other day) dose or as divided doses presented at appropriate intervals, for example as two, three, four, or more subdoses per day, or one dose every two, three, four, or five days.

For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an antibody against CD4, CD8, or CD40L. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., an antibody against CD4, CD8, or CD40L). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of an antibody against CD4, CD8, or CD40L with encapsulating material as a carrier providing a capsule in which the antibody (with or without other carriers) is surrounded by the carrier, such that the carrier is thus in association with the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an antibody against CD4, CD8, or CD40L) or sterile solutions of the active component in solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an antibody against CD4, CD8, or CD40L) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions one or more antibodies against CD4, CD8, or CD40L can be administered to a patient who have just received an transplant of cells, tissue, or organ in an amount sufficient to prevent, eliminate, reverse, or at least partially slow or arrest the symptoms of immune response such as rejection as well as its complications. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 1 mg to about 1000 mg per kg patient body weight, or about 5-500 mg/kg, about 10-100 mg/kg, about 20-50 mg/kg, e.g., about 10, 20, 25, 30, 40, 50, or 80, 100, 150, 200, or 300 mg/kg body weight for each antibody in each administration.

Single or multiple administrations of the compositions can be carried out with dose levels and pattern being selected by the treating physician. In any event, the pharmaceutical formulations should provide a quantity of the antibodies against CD4, CD8, and/or CD40L sufficient to effectively inhibit the undesired immune response such as transplant rejection in the patient. Typically, the administration starts immediately after the transplant procedure (e.g., on day zero) and lasts at least 1, 2, 3, 4, 5, 6, 7, 8, 9, 10 and up to 14 days on a daily or bi-daily (once every other day) schedule. In some cases, antibody administration may begin prior to the transplant procedure (day 0) from −10, −9, −8, −7, −6, −5, −4, −3, −2, and −1 day on a daily or bi-daily basis, in addition or in place of the post-transplant administration.

While an immune suppressant is generally not necessary to be co-administered to a recipient with the antibodies in order to induce immune tolerance, it is optional that one or more immune suppressants may be co-administered along with the antibodies, either in the same pharmaceutical composition(s) with the antibody or antibodies or in a separate pharmaceutical composition.

IV. Kits

The invention also provides kits for inducing immunotolerance according to the method of the present invention. The kits typically include a first container that contains a pharmaceutical composition having an antibody against CD4, a second container that contains a pharmaceutical composition having an antibody against CD8, optionally with a third container that contains a pharmaceutical composition having an antibody against CD40L. In some variations of the kits, a single container may contain a pharmaceutical composition having any two or all three of the antibodies against CD4, CD8, and CD40L. In the case of only two antibodies are present in one pharmaceutical composition in one container, typically the third antibody is present in another pharmaceutical composition in another container. Preferably, the pharmaceutical composition stored in each container contains each of the antibodies against CD4, CD8, and CD40L in an effective amount. The kits may further include informational material providing instructions on how to dispense the pharmaceutical composition(s), including description of the type of patients who may be treated (e.g., patients who have received stem cell transplant), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Results

Induction of Graft Acceptance to PSC-Derived Tissues.

It was previously reported that a combination of coreceptor (CD4 and CD8) and costimulation (CD40L) blockade was required to tolerize mice to fully histoincompatible skin grafts[13]. While costimulation blockade alone via the anti-CD40L monoclonal antibody (mAb) was insufficient to induce transplantation tolerance[17], coreceptor blockade alone was sufficient to induce acceptance of murine CBA/Ca ESC-derived embryoid bodies (EBs) in fully allogeneic C57Bl/6 [H-$2^b$] recipients (n=10, Table 1). These results expose some inherent capacity of ESC derived tissues to benefit from therapeutic protocols for tolerance induction. To enable acceptance of xenogeneic human PSC derived tissues, hESC-derived EBs were transplanted under the kidney capsule (not generally considered to be immunologically privileged) of outbred CD-1 mice following treatment with coreceptor and/or costimulation blockade (Table 1).

Figure 6:
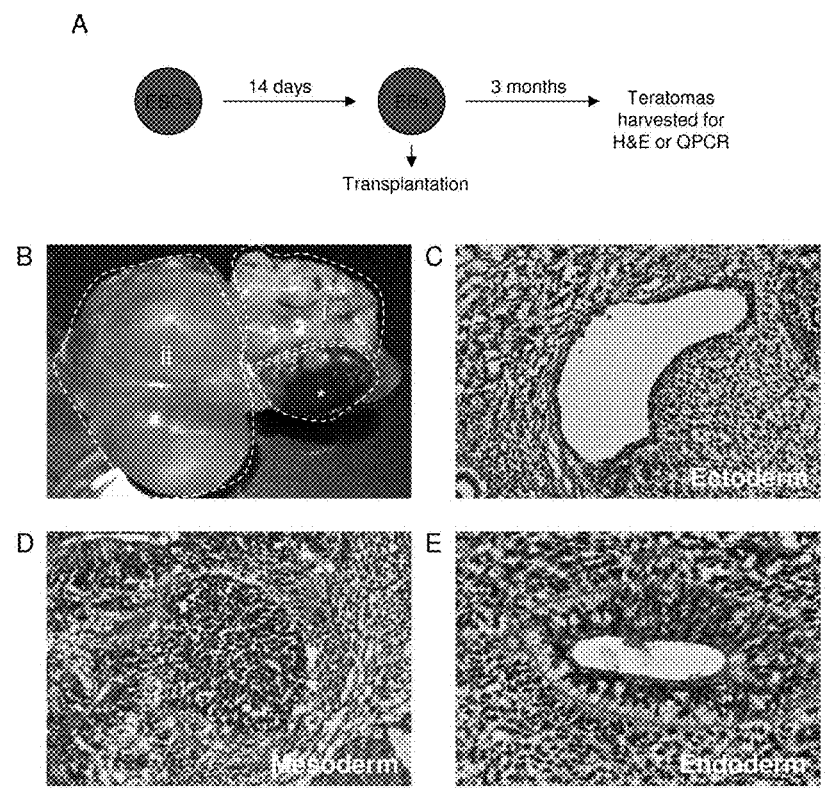
FIG. 6 Short-term coreceptor and costimulation blockade induces tolerance to pluripotent human ESCs. (A) Schematic diagram showing experimental approaches. (B) Representative image of hESC-derived teratomas formed 3 months post transplantation under the kidney capsule of CD-1 recipients following treatment with anti-CD4, -CD8 and -CD40L mAbs (n=5). (i) indicates teratoma tissues; (ii)

Unlike past experience with murine ESCs, coreceptor blockade alone was insufficient to induce tolerance to hESC-derived tissues (n=10, Table 1) and no graft elements remained by the end of 30 days post transplantation. hESC-derived EBs were accepted (n=30, Table 1) and differentiated into all three embryonic germ layers 90 days post transplantation (n=10, Table 2; FIG. 6) following treatment with combined coreceptor and costimulation blockade. FIG. 6b particularly demonstrates the engrafted elements following subrenal transplantation. Similarly, hiPSC-derived EBs were accepted 30 (n=10) or 90 (n=10) days post transplantation following treatment with both coreceptor and costimulation blockade (Table 2). No graft elements could be observed in the untreated group by the end of 30 or 90 days post transplantation.

Induction of Maturation to hESC-Derived Neural Progenitors.

Figure 1:
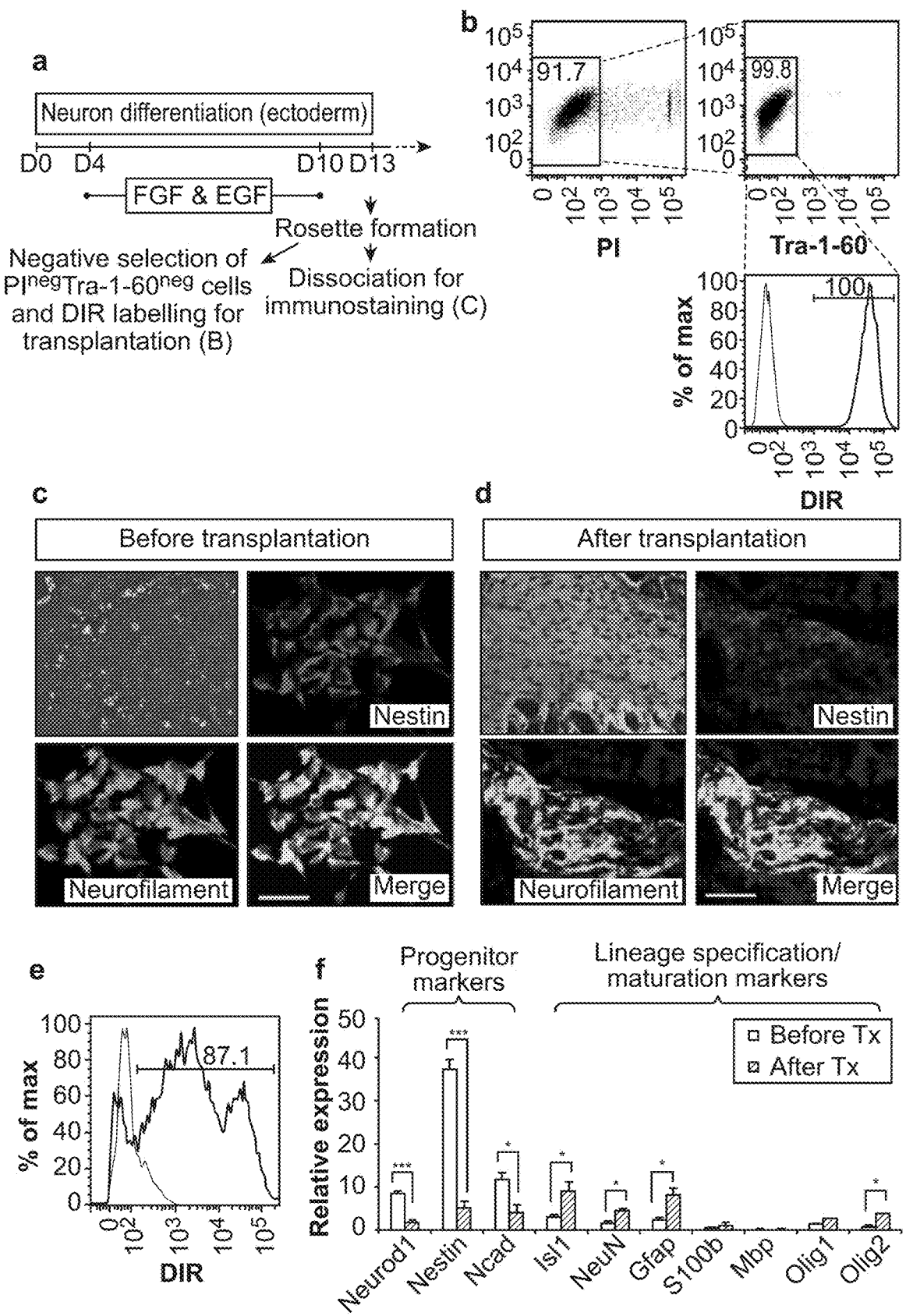
FIG. 1 Short-term coreceptor and costimulation blockade induces tolerance and maturation of human ESC-derived neural progenitor cells. (a) Differentiation protocol used to derive human neural progenitor cells. (b) Negative selection for PI$^-$ Tra-1-60$^-$ and positive selection for DIR$^+$ human neural progenitor cells by flow cytometry on day 13 of human ESC differentiation. (c) A representative live image and immunostaining of human neural progenitor cells with neural cell-specific markers nestin (red), neurofilament (green) and DAPI (blue) on day 13 of differentiation (n=5). Scale bar, 25 µM. (d) Frozen sections of human neural cells transplanted under the kidney capsule of CD-1 mice for 30 days following treatment with anti-CD4, -CD8 and -CD40L mAbs. Sections were stained with nestin (red), neurofilament (green) and DAPI (blue). Scale bar, 50 µM. (e) Purification of DIR$^+$ human neural cells by flow cytometry on day 30 of transplantation. (f) Quantitative RT-PCR of DIR$^+$ human neural cells on day 30 of transplantation; expression levels of the progenitor or terminally differentiated cell markers were compared with that of undifferentiated hESCs (value on y axis=1). Data are presented as mean±s.d. *P<0.05 and ***P<0.005.

Since the accepted EBs formed teratomas in vivo that consisted of ectoderm-like cells (FIG. 6c), it was examined whether the short-term tolerizing protocol could enable acceptance of human neural progenitor cells of the ectoderm lineage. hESCs were directed to differentiate into neural progenitor cells with EGF and FGF2 using a protocol (FIG. 1a) modified from previous reports[18]. hESC-derived neural progenitor cells were isolated from neural rosettes and labelled with the DIR dye for human cell tracking after transplantation. These cells were also stained with propidium iodide (PI) and Tra-1-60, and the PI$^-$ DIR$^+$ Tra-1-60$^-$ population was purified by flow cytometry to prevent contamination with PI$^+$ dead cells and formation of teratomas by Tra-1-60$^+$ undifferentiated hESCs before transplantation (FIG. 1b). To confirm cell identity at the end of directed differentiation, immunostaining (FIG. 1c) and quantitative reverse transcription PCR (RT-PCR; FIG. 1f) were performed to check for expression of neural progenitor cell-specific markers including nestin, neurofilament, neurogenic differentiation 1 (Neurod1) and N-cadherin (NCad). The results confirmed that all the transplanted hESC-derived neural progenitor cells were nestin$^+$ neurofilament$^+$ before transplantation (FIG. 1c). The PI$^-$ DIR$^+$ Tra-1-60$^-$ nestin$^+$ neurofilament$^+$ human neural progenitor cells were transplanted under the kidney capsule of CD-1 mice following three injections of anti-CD4, -CD8 and -CD40L mAbs within the first week post transplantation and graft acceptance was monitored at day 30, 90 and 180 post transplantation. The grafted human neural progenitor cells survived for 1 month (n=30), 3 months (n=10) and 6 months (n=6) following only three doses of coreceptor and costimulation blockade in the first week post transplantation (Table 2). As no graft remains could be detected in the untreated group, no further analyses could be applied at 1 month post transplantation in the control group.

To confirm cell identity at the end of study, grafts were harvested and nestin$^+$ neurofilament$^+$ human cells were observed in the graft sites 30 days post transplantation (FIG. 1d). It has been reported that conventional immunosuppressants such as cyclosporine and dexamethasone strongly inhibit terminal differentiation of neural progenitor cells into mature neurons[10]. To examine whether our tolerizing protocol allows terminal differentiation and maturation of the grafted human neural progenitor cells, grafts were dissociated with liberase and DIR$^+$ cells were purified by flow cytometry (FIG. 1e) for subsequent analyses with quantitative RT-PCR. The human gene expression analyses showed that the grafted cells downregulated neural progenitor cell-specific genes (Neurod1, nestin, NCad) and upregulated neuron-specific genes (Isl1, NeuN), astrocyte-specific gene (Gfap) and glial cell-specific genes (Olig1, Olig2) at 30 days post transplantation compared with that of hESC-derived neural progenitor cells before transplantation (FIG. 1f). The gene expression pattern revealed that multiple cell lineages of the neuron system (neurons/astrocytes/glial cells) had spontaneously differentiated from the grafted human neural progenitor cells in vivo.

Induction of Maturation to hESC-Derived Endothelial Progenitors.

Figure 2:
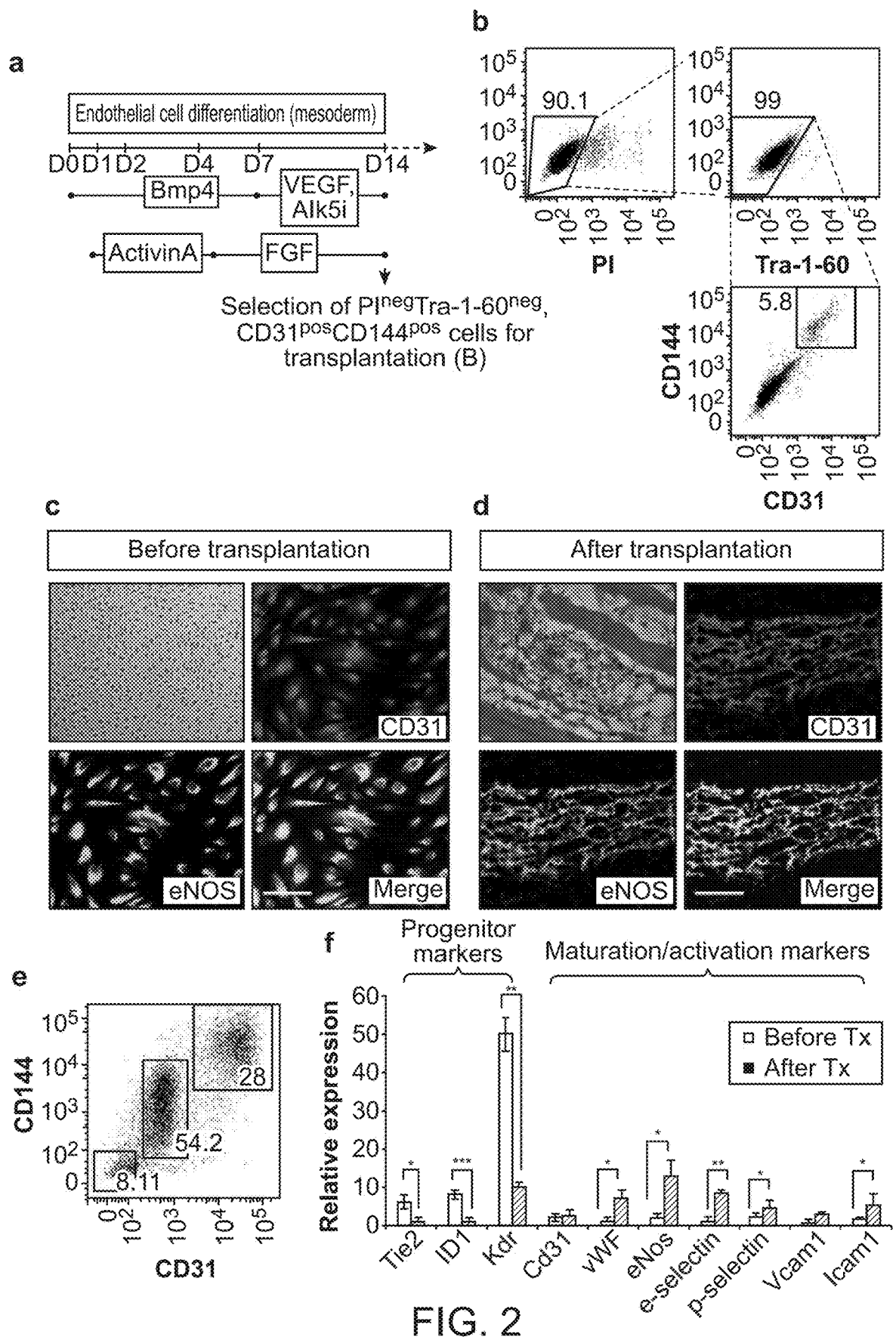
FIG. 2 Short-term coreceptor and costimulation blockade induces tolerance and maturation of hESC-ECs. (a) Differentiation protocol used to derive human endothelial progenitor cells. (b) Negative selection for PI$^-$ Tra-1-60$^-$ and positive selection for DIR$^+$ human endothelial progenitor cells by flow cytometry on day 13 of human ESC differentiation. (c) A representative live image and immunostaining of endothelial progenitor cells with endothelial cell-specific markers CD31 (red), eNOS (green) and DAPI (blue) on day 14 of differentiation (n=5). Scale bar, 25 µM. (d) Frozen sections of human endothelial cells transplanted under the kidney capsule of CD-1 mice for 30 days following treatment with anti-CD4, -CD8 and -CD40L mAbs. Sections were stained with CD31 (red), eNOS (green) and DAPI (blue). Scale bar, 50 µM. (e) Purification of CD31$^+$ CD144$^+$ human endothelial cells by flow cytometry on day 30 of transplantation. (f) Quantitative RT-PCR of CD31$^+$CD144$^+$ human endothelial cells using anti-human CD31 and CD144 mAbs on day 30 of transplantation; expression levels of the progenitor or activation markers were compared with that of undifferentiated hESCs (value on y axis=1). Data are presented as mean±s.d. *P<0.05, P<0.01 and *P<0.005.

Since the tolerized EBs formed teratomas in vivo that consisted of mesoderm-like cells (Supplementary FIG. 1d), it was examined whether the tolerizing protocol could enable acceptance of human endothelial cells of the mesoderm lineage. hESCs were directed to differentiate into endothelial progenitor cells (FIG. 2a), modified from our previous report[19]. At the end of directed differentiation, cells were stained with PI and Tra-1-60 and with endothelial cell-specific markers, CD31 and CD144 (FIG. 2b). The PI$^-$ Tra-1-60$^-$ CD31$^+$ CD144$^+$ hESC-derived endothelial progenitor cell (hESC-ECs) population was purified by flow cytometry to prevent contamination with PI$^+$ dead cells and formation of teratomas by Tra-1-60$^+$ undifferentiated hESCs before transplantation (FIG. 2b). To confirm cell identity at the end of directed differentiation, immunostaining (FIG. 2c) and quantitative RT-PCR (FIG. 2f) were also performed to check for expression of endothelial progenitor cell-specific markers including CD31, endothelial nitric oxide synthase (eNOS), Tie2, Id1 and VEGF receptor (Kdr). The results confirmed that all the transplanted hESC-ECs were CD31$^+$ eNOS$^+$ before transplantation (FIG. 2c). The PI$^-$ Tra-1-60$^-$ CD31$^+$ CD144$^+$ eNOS$^+$ hESC-ECs were transplanted subcutaneously (s.c.) into CD-1 mice following three injections of anti-CD4, -CD8 and -CD40L mAbs within the first week post transplantation and graft acceptance was monitored at day 30 and 90 post transplantation. The grafted human endothelial progenitor cells survived for at least 3 months following this brief induction protocol (FIG. 7).

To confirm cell identity at the end of study, grafts were harvested and CD31$^+$ eNOS$^+$ human cells were observed in the graft sites 30 days post transplantation (FIG. 2d). To examine whether the tolerizing protocol allows terminal differentiation and maturation of the grafted human endothelial progenitor cells, grafts were dissociated with liberase and stained with anti-human (h) CD31 and hCD144 mAbs. CD31$^+$ CD144$^+$ cells were then purified by flow cytometry (FIG. 2e) for subsequent analyses with quantitative RT-PCR. Human gene expression analyses showed that the grafted cells expressed less endothelial progenitor cell specific genes (Tie2, Id1, Kdr) but more activated and mature endothelial cell-specific genes (vwf, e-selectin, p-selectin, Vcam1, Icam1) 30 days post transplantation compared with that of hESC-ECs before transplantation (FIG. 2f). To examine whether the tolerizing protocol allows long-term survival of the grafted hESC-ECs, grafts were harvested and vascular structures were examined by histology 90 days post transplantation (FIG. 7a,b). In addition, grafts were stained with anti-hCD31, -hCD144, -vWF and -eNOS mAbs, which are endothelial cell-specific markers (FIG. 7c,f).

Induction of Tolerance in a Tissue-Specific Manner.

It was previously shown that, within tolerant hosts, CD4$^+$ FoxP3$^+$ Treg are constantly vigilant in suppressing effector T cells capable of rejecting murine skin[13]. In the present study, all hESC-derived neural progenitor cells survived for at least 30 days after subcutaneous transplantion into the same CD-1 recipients that had accepted neural progenitor cells derived from the same hESC line (H9) 120 days ago (n=6, Table 3). Similarly, all hESC-ECs survived for at least 30 days after subcutaneous transplantation into the same CD-1 recipients that had accepted neural progenitor cells derived from the same hESC line (H9) 120 days previously (n=6, Table 3), suggesting that once tolerance had been established it was sufficient to guarantee survival of a second graft of a different tissue type derived from the same donor hESCs, without further immunosuppression.

Figure 3:
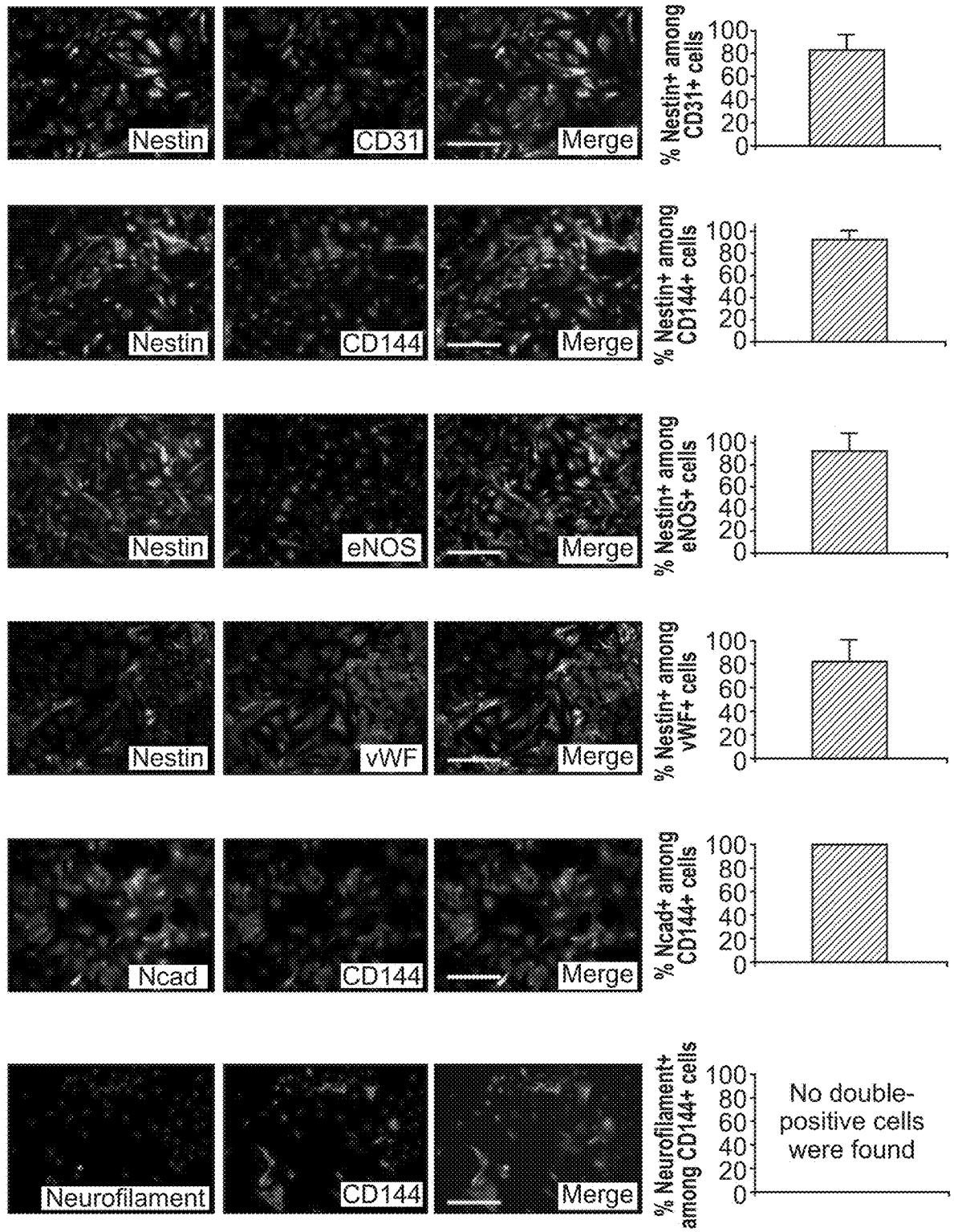
FIG. 3 Expression of common antigens by hESC-ECs. (a) Immunostaining of neural cell-specific markers (green) and endothelial cell-specific markers (red) expressed by CD31$^+$ CD144$^+$ endothelial progenitor cells on day 14 of human ESC differentiation (n=5). Scale bar, 50 µM. (b) Quantitative RT-PCR of neural progenitor cells or CD31$^+$CD144$^+$ endothelial progenitor cells on days 13-14 of differentiation; expression levels of the neural cell specific or endothelial cell-specific genes, respectively, were compared with that of undifferentiated hESCs (value on y axis=1). Data are presented as mean±s.d.
Figure 3:
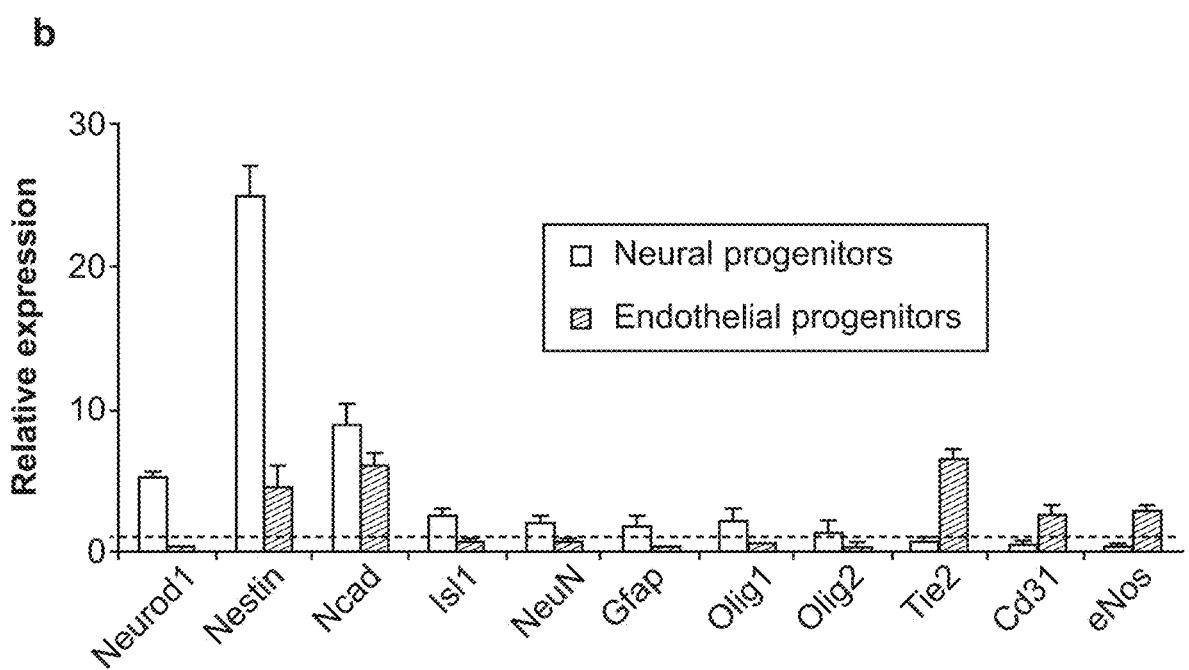

To determine whether acceptance of hESC-ECs was a result of antigen recognition during tolerance induction to the primary neural grafts, the primary grafts were stained with both neural (nestin) and endothelial (CD31, CD144, eNOS, vWF) cell-specific antigens (FIG. 8). Importantly, the primary grafts did not express endothelial cell-specific markers that, therefore, would not have been seen during the tolerization window. To confirm that the second graft expressed a range of antigens in common with the primary graft, hESC-ECs were also stained with both endothelial (CD31, CD144, eNOS, vWF) and neural (nestin, NCad, neurofilament) cell-specific markers before transplantation (FIG. 3a). Intriguingly, all endothelial progenitor cells also expressed known neural progenitor cell-specific antigens nestin and NCad. It is worth noting that the same batches of antibodies were used for FIGS. 2 and 3, indicating that the negative results on CD31, CD144, eNOS and vWF expression in FIG. 8 were not due to non-functional antibodies. Quantitative RT-PCR was performed to compare neural (Neurod1, nestin, Ncad, Isl1, NeuN, Gfap, Olig1, Olig2) and endothelial (Tie2, Cd31, eNos) gene expressions between neural and endothelial progenitor cells (FIG. 3b). The results were consistent with that of immunostaining, which showed that endothelial cell progenitors expressed nestin and Ncad as common antigens with neural progenitor cells. This sampling of common antigens between two tissues derived from identical host hESCs allows the proposal that linked suppression towards many shared antigens, when presented on host antigen-presenting cells, could account for acceptance of the heterologous tissue types by tolerant hosts.

To examine whether the established tolerance was sufficient to maintain survival of a second graft of diverse tissue types derived from the same donor hESCs, or of the same tissue type derived from a different donor of hESCs, EBs derived from the same parental hESC line (H9) or neural progenitor cells derived from a different donor hESC line (H1) were subcutaneously transplanted 90 days following transplantation of hESC derived neural progenitor cells (H9). While the primary grafts remained intact 90 days following transplantation, all the H9 hESC-derived EBs and H1 hESC-derived neural progenitor cells were rejected 30 days post transplantation (n=6 in each group, Table 3), suggesting that tolerance induction through coreceptor and costimulation blockade is relatively tissue antigen-specific and acceptance of the second graft depends on the types and numbers of antigen difference from the primary graft.

A Shift from Effector T Cell to Treg Graft Infiltration.

Figure 4:
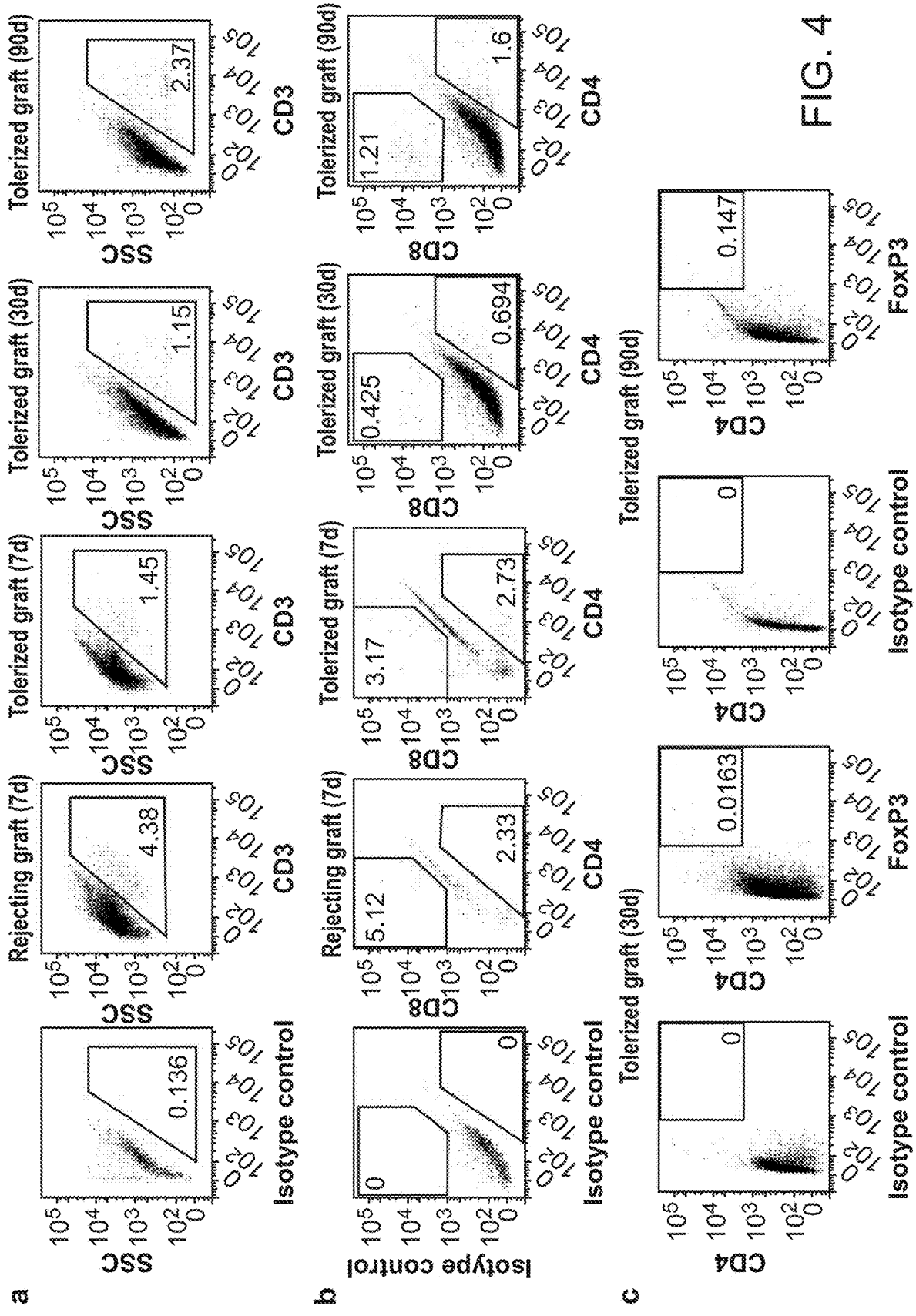
FIG. 4 Tolerized grafts of hESC-derived neural cells display less infiltrating effector T cells but more infiltrating regulatory T cells. (a) Representative plots of flow cytometry showing intragraft infiltration of CD3$^+$ T cells transplanted under the kidney capsule of untreated recipients (rejecting grafts) or anti-CD4, -CD8 and -CD40L mAb-treated recipients (tolerized grafts) at the indicated time point of transplantation (n=3). (b) Representative plots of flow cytometry showing intragraft infiltration of CD8$^+$ or CD4$^+$ T cells transplanted under the kidney capsule of untreated recipients or mAb-treated recipients at the indicated time point of transplantation (n=3). (c) Representative plots of flow cytometry showing infiltration of CD4$^+$FoxP3$^+$ T cells in grafts transplanted under the kidney capsule of mAb-treated recipients at the indicated time point of transplantation (n=3).

The T-cell response against the tolerized xenografts derived from mAb-treated recipients was compared versus rejecting xenografts derived from the same strain of untreated recipients. To examine whether coreceptor and costimulation blockade had an effect on the quantity and type of infiltrating T cells as an indicator of immunoregulation[7,8], rejecting or tolerized neural progenitor cells were dissociated at the indicated time points with liberase and stained with CD3, CD4 or CD8 antibodies for flow cytometric analyses. The results showed that there were more infiltrating CD3+ cells in the rejecting grafts at day 7 (4-6% of total cells, n=6) post transplantation compared with that of the tolerized grafts at day 7 (0.5-1.5%, n=6), 30 (0.5-1.3%, n=6) and 90 (2-3%, n=6) post transplantation (FIG. 4a). Specifically, there were also more infiltrating CD8+ cells in the rejecting grafts at day 7 (5-6%, n=6) post transplantation compared with that of the tolerized grafts at day 7 (2.5-3.5%, n=6), 30 (0.2-0.8%, n=6) and 90 (1-1.5%, n=6) post transplantation (FIG. 4b). Interestingly, the proportion of infiltrating CD4+ cells was greatest at an earlier time point (day 7) in both the rejecting and tolerized grafts compared with later time points (days 30 and 90) in the tolerized grafts (FIG. 4b), although grafts were no longer present at later time points (days 30 and 90) in the rejecting recipients.

To search for any possible role of tissue-infiltrating Treg in graft acceptance, the proportion of CD4+FoxP3+ Treg in spleens (a secondary lymphoid organ) and grafts of the tolerized recipients was quantified by flow cytometry. Although FoxP3 alone might not be able to locate all Treg, it was previously demonstrated in multiple studies that FoxP3 is the most reliable marker to determine Treg localization and function[7,8,13]. As shown in FIG. 9, the proportion of CD4+FoxP3+ cells in spleens of the tolerized recipients was comparable to that of spleens of untreated mice. However, infiltrating CD4þFoxP3þ cells were observed in the tolerized grafts at days 30 and 90 post transplantation (FIG. 4c). These results were consistent with our previous studies where we found infiltrating Treg in the tolerized graft at days 30 (refs 7,8) and 90 (refs 20,21) post transplantation, suggesting that combined coreceptor/costimulation blockade may have enabled Treg to accumulate in the tolerized tissue. It is also interesting to note that there were more infiltrating CD8+ and CD4+ cells in the tolerized grafts at day 90 compared with day 30 (FIG. 4b), but also more CD4+FoxP3+ Treg in the tolerized grafts at day 90 compared with that at day 30 (FIG. 4c) post transplantation, not inconsistent with the possibility that tissue Treg were maintaining constant vigilance in keeping the peace in the accepted tissues[13].

Gene Expression Profiling of Tissues and CD3+ Lymphocytes.

Figure 5:
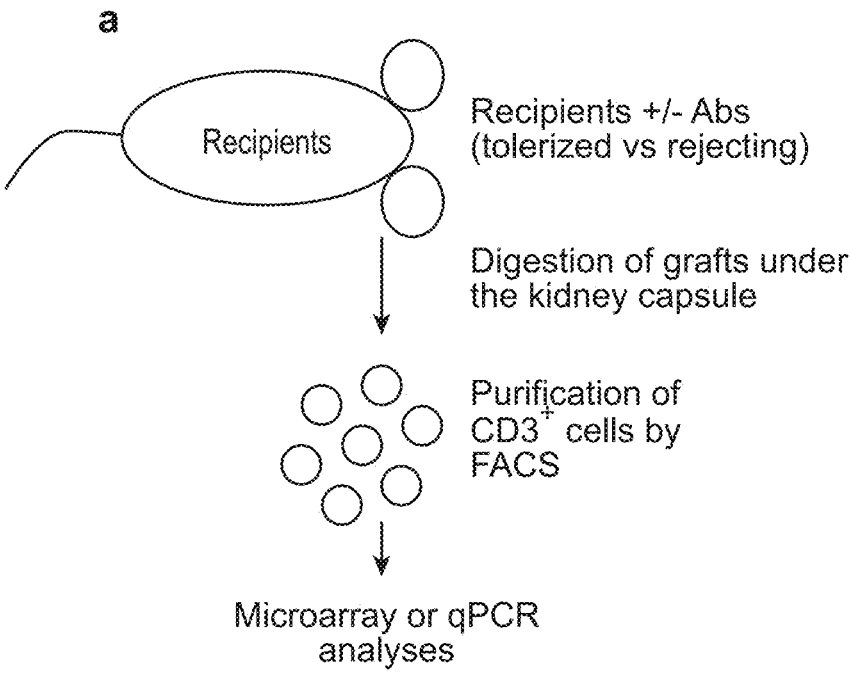
FIG. 5 Gene expression profiling of tissues and their infiltrating CD3$^+$ T cells during immunoregulation. (a) Schematic diagram of experimental design. (b) Results of microarray analyses showing normalized enrichment score of CD3$^+$ cells isolated from the tolerized grafts compared with that of the rejecting grafts. (c,d) Top 50 most differentially expressed genes (c) upregulated or (d) downregulated in CD3$^+$ cells isolated from the tolerized grafts compared with that of the rejecting grafts. (e,f) Quantitative RT-PCR of CD3$^+$ cells isolated from untreated recipients (rejecting grafts) or anti-CD4, -CD8 and -CD40L mAb-treated recipients (tolerized grafts) on day 30 of transplantation; their expression levels of (e) pro-inflammatory or (f) anti-inflammatory cytokines were compared with that of cells isolated from an empty matrigel plug transplanted in untreated mice to capture resting infiltrates (value on y axis=1). (c,d) Quantitative RT-PCR of DIR$^+$ human neural cells isolated from untreated recipients (rejecting grafts) or anti-CD4, -CD8 and -CD40L mAb-treated recipients (tolerized grafts) on day 30 of transplantation; their expression levels of (g) pro-inflammatory or (h) anti-inflammatory cytokines were compared with that of undifferentiated hESCs (value on y axis=1). Data are presented as mean±s.d. *P<0.05, P<0.01 and *P<0.005.
Figure 5:
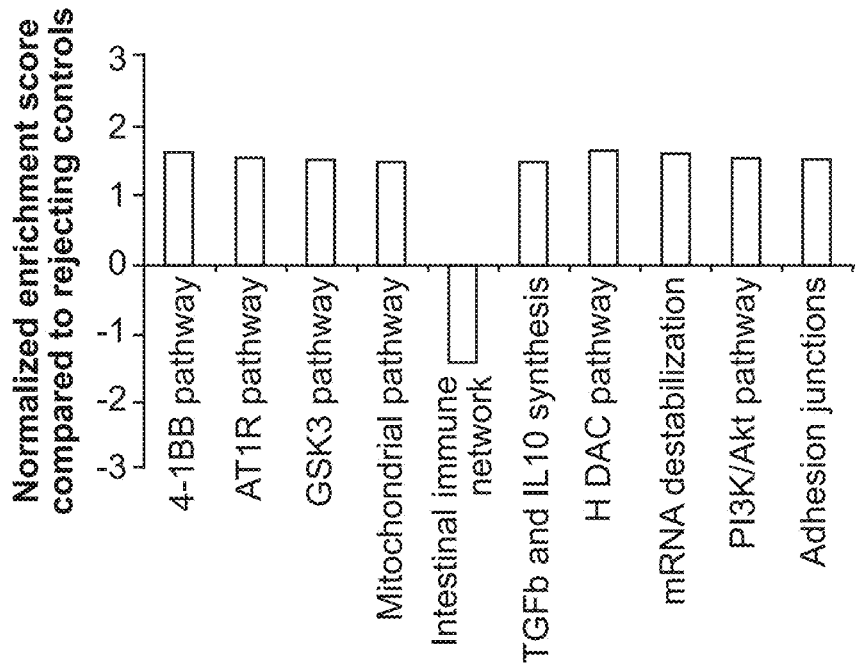

Certain genetic profiles have been previously described for anergic[15,22] and regulatory T cells[23-25] during the course of wound healing, autoimmunity and tolerance induction. To examine the underlying mechanisms for immune regulation during tolerance induction to hESC-derived tissues, global gene expression profiles of CD3+ cells purified from xenografts of untreated recipients (rejecting) or recipients treated with combined coreceptor and costimulation blockade (tolerized) were analysed by microarrays and quantitative RT-PCR 30 days post transplantation (FIG. 5a). Results from gene set enrichment analysis (GSEA) showed that the two populations were clearly different. Genes associated with a number of immunological and metabolic pathways were significantly enriched in the tolerance-associated group (FIG. 5b). There were 50 genes significantly upregulated (FIG. 5c, P<0.001) and 50 others downregulated (FIG. 5d, P<0.001), respectively, in CD3+ cells purified from xenografts of tolerized recipients compared with those of the rejecting recipients. There were genes both upregulated and downregulated by tolerized T cells in each of these pathways, suggesting a mixed population of T cells within the total CD3+ population. Specifically, CD3+ cells isolated from tolerized recipients showed a significant upregulation of genes (P<0.05) involved in apoptosis (mitochondrial pathway), cell adhesion, mRNA destabilization (by KSRP, BRF1 or tristetraprolin) and TGFb/IL10 synthesis (intestinal immune network for IgA production) compared with that of the rejecting controls (Table 4a). Also, CD3+ cells isolated from tolerized recipients showed a significant downregulation of genes (P<0.05) involved in inflammation (4-1BB-dependent tumour-necrosis factor (TNF) receptor pathway such as NFkB, Ifng, Il2) compared with that of the rejecting controls (Table 4b). Furthermore, quantitative RT-PCR was performed to confirm gene expression profiles of pro-inflammatory and anti-inflammatory cytokines expressed by $CD3^+$ T cells purified from xenografts of rejecting or tolerized recipients. There were significantly lower expression levels of Il2, Ifna and Tnfa (P<0.01, FIG. 5e), but significantly higher expression levels of Il10 and Tgfb1 (P<0.05, FIG. 5f) in $CD3^+$ T cells isolated from the tolerized grafts compared with that of rejecting xenografts. Finally, to assess the overall inflammatory states of the transplanted grafts, we have also performed quantitative RT-PCR to examine gene expression profiles of pro-inflammatory, anti-inflammatory and regulatory cytokines expressed by xenografts of the rejecting or tolerized recipients. It was found that there were significantly lower expression levels of genes for pro-inflammatory cytokines (P<0.01, FIG. 5g), particularly Il2, Il12b, Il17a and Ifna, but significantly higher expression levels of anti-inflammatory and regulatory cytokine genes (P<0.05, FIG. 5h), particularly Il10, Tgfb1, Tgfb2 and Tgfb3, in the tolerized xenografts compared with that of the rejecting xenografts. Although there was a slight difference in expression levels of genes between the cysts and teratomas, comparable patterns could be observed in the majority of genes of pro-inflammatory (FIG. 10), anti-inflammatory and regulatory cytokines (data not shown) between tolerized and rejecting xenografts of hESC-derived EBs.

Discussion

The critical shortage of donor organs for treating end-stage organ failure emphasizes the need for deriving tissue organs from hPSCs, predominantly hiPSCs, for transplantation. Recent advances show that a vascularized and functional human liver can be generated from hiPSCs by transplanting hiPSC-derived liver buds into immunocompromised murine recipients[1]. Although autologous transplantation with self hiPSC-derived tissues would be ideal, more work is still needed to rule out immunogenicity of such cells resulting from their reprogramming, differentiation and engraftment into autologous recipients. Nevertheless, allogeneic hESC-derived progenitor cells/tissues will likely be used for clinical transplantation, particularly in conditions involving acute injuries[4,5,19,26,27]. It was reported previously that ESC-derived tissues can acquire immune privilege by recruiting antigen-specific Treg to ensure their spontaneous acceptance across minor[8] or class-I major[7] histocompatibility barriers. This facility to acquire immune privilege likely contributes to the finding that, for the first time, a short-term antibody-based protocol has proven able to achieve long-term tolerance to hESC-derived neural or endothelial progenitor cells in murine hosts. This protocol ensured long-term acceptance, continued differentiation and maturation of hESC-derived progenitor cells in vivo, in a xenotransplantation setting, such acceptance associated with an enhanced presence of $CD4^+FoxP3^+$ Treg in the tolerized grafts.

Although it is clearly beneficial to be able to transplant human progenitor cells capable of self-renewing or differentiating into multiple cell types of interest, hESC-derived progenitor cells pose a special challenge for tolerance induction because their diverse differentiated progenies will express different sets of lineage specific and maturation antigens distinct from those of parental progenitor cells. For instance, it has been shown that the transplanted neural progenitor cells newly expressed Olig2 on 30-day differentiation in vivo (FIG. 1f), and transplanted endothelial progenitor cells expressed e-selectin, p-selectin, ICAM1 and VCAM1 on 30-day differentiation and activation in vivo (FIG. 2f). Such antigens were absent in their parental progenitor cell state before further lineage commitment[19] or activation by stimuli[28,29] such as cytokines or growth factors in vivo. Therefore, any tolerance induced to the parental progenitor cells would need to be extended to their differentiated progenies as a collateral benefit via linked suppression and infectious tolerance[11-14,30]. Induced or peripheral Treg (pTreg) could, in principle, mediate linked suppression and amplify themselves through infectious tolerance[31], allowing protection of subsequent committed and more mature grafts by exploiting the same set of antigens (common antigens) expressed by both progenitor cells and differentiated progenies. In this study, the present inventors gave examples of such common antigens demonstrating that both the neural progenitor cells and their differentiated progenies expressed nestin and neurofilament and both the endothelial progenitor cells and their differentiated progenitors expressed CD31 and eNOS.

Another advantage of using hPSC-derived tissues for CRT is that recipients could receive a second graft without needing additional immunosuppression, given that linked suppression would be sustained by self-renewing, antigen-specific Treg. Importantly, the inventors have demonstrated that recipients accepted a second graft of the same tissue type derived from the same donor hESCs (H9 hESC-derived neural progenitor cells) 90 days following transplantation of the primary graft (H9 hESC-derived neural progenitor cells) without additional immunosuppression, demonstrating that tolerance had been established to hESC-derived tissues by combined coreceptor and costimulation blockade. A 90-day readout was chosen to avoid residual immunosuppressive effects of the initial tolerizing treatment[13,14,32]. This is consistent with the previous findings that tolerance to murine skin grafts required continuous availability of donor antigens to maintain it[14,33]. In the present study, the present inventors performed a series of transplants with different sources of secondary grafts to further determine the extent to which tolerance induced to the primary graft could also protect a secondary graft of a different tissue type derived from the same donor hESCs, a combination of different tissue types derived from the same donor hESCs, or the same tissue type derived from an unrelated donor. Their data indicate that tolerance can be extended to a secondary graft of a different tissue type derived from the same donor hESCs, but not from a different major histocompatibility complex (MHC)-mismatched donor. When recipients were tolerized to H9 hESC-derived neural progenitor cells (primary graft), H9 hESC-derived endothelial cells (second graft) could also survive for at least 30 days without any additional immunosuppression. It has been demonstrated that the primary neural graft does not express certain antigens considered unique to the subsequent endothelial graft. Therefore, antigens of the second graft should not have been recognized during tolerance induction to the primary graft; however, the second endothelial graft did express some antigens in common with the primary neural graft, for example, nestin and NCad. Antigens such as these might provide the basis for linked suppression extending to the unique antigens.

It is conceivable that the data could be explained by the primary graft having retained a minor pluripotent population, which could theoretically have provided a source of diverse cell types and their tissue-specific antigens, during the phase of tolerance induction. In such a scenario, the second graft would have been accepted as its antigens should have been recognized during the tolerization phase. Against this though, tolerized hosts rejected secondary grafts of a combination of tissue types derived from the same donor hESCs (H9 hESC-derived EBs), indicating that they could not be tolerant to all H9 hESC-derived antigens. The host also rejected a secondary graft of the same tissue type derived from a histoincompatible allogeneic donor (H1 hESC derived neural progenitor cells), indicating that they still had the ability to reject xenogeneic antigens and that there was an element of antigen specificity to tolerance. If tolerance is mediated through linked suppression, then any collateral benefit would be dependent on the degree of similarity in the type and amount of antigens expressed by both the primary and secondary grafts.

To determine the underlying mechanisms of tolerance induction to hESC-derived tissues by coreceptor and costimulation blockade, CD3+ T cells were isolated from tolerized (treated) or rejecting (untreated) grafts for global gene expression analyses. The results might indicate that a mixed population of CD3+ T cells was present in the tolerant group, one expressing anti-apoptotic (upregulation of Bcl2 and downregulation of Bak or Bid) and the other expressing pro-apoptotic genes (upregulation of caspases). In general, the inventors found that certain pathways appeared to be associated with tolerance compared with that of the rejecting controls: CD3+ cells isolated from tolerized recipients showed a significant upregulation of genes involved in apoptosis, cell adhesion and mRNA destabilization via epigenetic regulation, and syntheses of anti-inflammatory cytokines such as TGFb and IL10 ($P<0.05$). On the other hand, CD3+ cells isolated from tolerized recipients showed a significant downregulation of genes involved in inflammation, particularly the 4-1BB-dependent TNF receptor pathway (NfKB, Tnfa Ifng, Il2; $P<0.05$). In addition to CD3+ cells within the grafts, tissue cytokine profiling has also been performed with the tolerized or rejecting grafts and found that tolerized tissues expressed lower levels of pro-inflammatory (Il2, Il12b, Il17a, Ifng) but higher levels of anti-inflammatory and regulatory cytokines (Tgfb1, Tgfb2, Tgfb3 and 1110) compared with that of the rejecting grafts ($P<0.05$). Interestingly, the tolerized tissues predominantely expressed Tgfb3, while CD3+ cells predominantely expressed Tgfb1 and Il10 as protective cytokines consequent to tolerance induction. These results were also consistent with the previous findings that hESC-derived tissues expressed Tgfb3, perhaps reflecting an additional privilege-associated mechanism contributing to the induction de novo of pTreg[7,8].

Foxp3+ Treg are essential for self-tolerance as multiple autoimmune diseases develop in their absence[34]. In certain circumstances where tolerance is induced therapeutically, Treg have been shown to be constantly required to suppress effector T cells that are otherwise capable of causing tissue damage[13]. Foxp3+ Treg have been shown to be empowered to maintain tolerance achieved by coreceptor and/or costimulation blockade across all levels of histocompatibility mismatch: full MHC[13], a single MHC[7], multiple minor[35] and a single minor[8,21] antigen in allogeneic murine recipients. In one study, we have also shown that coreceptor blockade induced tolerance to rat xenografts in murine recipients[36]. Nevertheless, this study provides the first demonstration of tolerance induction to xenogeneic hESCderived tissues by coreceptor and costimulation blockade. This might be expected if one assumes the bulk of antigen presentation for regulation was indirect[9,30], giving new insights into tolerance induction to xenogeneic stem cell transplantation.

Strategies capable of harnessing Treg in man could then be of value to promote acceptance of human stem cell transplants. Although the equivalent coreceptor and costimulatory antibodies are not yet licensed for clinical use, there are other similar approaches to selectively harness Treg that may be of more immediate clinical relevance. For example, the more established mixed chimerism approach pioneered by Sachs and Sykes[37] has already provided some evidence that Treg may be contributing to graft acceptance, at least in some patients. Similarly, lymphocyte depletion with agents such as alemtuzumab, followed by short term antibody therapy to guide reconstitution of the repopulating cells could also offer a clinically applicable approach[38]. Moreover, recent advances in developing drug-minimization protocols by the use of alemtuzumab combined with a short period of costimulation blockade via belatacept and mTOR inhibition promote acceptance of renal grafts without impediment to Treg function in man[39]. Nevertheless, the current study focused on the competing role(s) of effector T cells and Treg during tolerance induction to stem cell grafts. The results highlight the need for further mechanistic studies to fully explain mechanisms of linked suppression and acquired privilege that operate in this form of therapeutic tolerance. In summary, these pre-clinical findings suggest that development of tolerizing protocols for regenerative medicine and CRT should focus on patient-friendly ways of exploiting Treg, in a manner that ensures continued differentiation and maturation of human stem cell grafts following establishment of transplantation tolerance.

Methods

Mouse ESC Cultures and EB Differentiation.

The ESF116 ESC line was derived from male CBA/Ca mice as reported previously[7]. ESF116 ESCs were maintained in ES medium containing Dulbecco's Modified Eagle's Medium (Cambrex Bio Science Verviers), 15% v/v fetal calf serum (FCS; Gibco), 50 µg ml$^{-1}$ penicillin and streptomycin, 1 mM sodium pyruvate, 2 mM L-glutamine and 50 mM 2-mercaptoethanol. Before differentiation, ESCs were passaged twice on gelatin and cultured in ES medium supplemented with 1,000 U ml$^{-1}$ recombinant leukaemia inhibitory factor (rLIF; Millipore). EBs were formed from 500 ESCs per 20 ml in hanging drop cultures in the absence of rLIF for 2 days and individual EBs were then transferred to suspension cultures for another 12 days before transplantation.

Human ESC Cultures and Lineage-Specific Differentiation.

The H9 human ESC (Wicell) and human iPSC lines (a gift from Dr Gustavo Mostoslaysky, Department of Medicine, Boston University, USA) were maintained in mTseR1 medium (Stemgent). hESCs were differentiated into derivatives of the three embryonic germ layers by stepwise administration of growth factors as described previously[18,19]. Briefly, for neural cell induction, hESCs were grown in clusters with neural differentiation medium containing 50% Neurobasal, 50% DMEM/F12, 2% B27 and 1% N2 (Gibco) for 4 days. Small clumps of neuroectodermal spheres were then cultured with 20 ng ml$^{-1}$ FGF2 and 20 ng ml$^{-1}$ EGF (R&D) for 6 days. After that, the spheres were replated on 10 µg ml$^{-1}$ laminin-coated plates and cultured for 3 days to form rosettes. For endothelial cell induction, hESCs were cultured with hESC differentiation medium containing DMEM/F12, 10% knockout serum replacement (KOSR), 1× non-essential amino acids, 1× glutamine, 1× penicillin/streptomycin and 1× b-mercaptoethanol (Gibco) for 4 days. The differentiated cells were then replated in matrigel-coated plates and cultured in hESC differentiation medium containing 1% KOSR for 10 days under hypoxia (5% oxygen). A combination of growth factors was supplemented as follows: 20 ng ml$^{-1}$ BMP4 (R&D, day 0-7), 10 ng ml$^{-1}$ activinA (R&D, day 1-4), 10 ng ml$^{-1}$ FGF2 (Peprotech, day 4-14) and 100 ng ml$^{-1}$ VEGF-A (Peprotech, day 7-14). For EB induction, hESCs or hiPSCs were resuspended in hESC differentiation medium containing 10% KOSR in hanging drop cultures for 2 days. Individual EBs were then transferred to suspension cultures and incubated in hESC differentiation medium containing 1% KOSR for another 12 days before transplantation.

Preparation of Cells for Transplantation.

To generate cells for transplantation, single cells were isolated using 0.25% trypsin-EDTA and stained with PI (BD) to exclude dead cells. hESC-derived neural cells were stained with fluorochrome conjugated anti-Tra-1-60 antibody (BD, dilution 1:100) and purified on FACS AriaII (BD) to exclude the undifferentiated pluripotent stem cells. The purified PI$^-$ Tra-1-60$^-$ cells were then labelled with DIR dye (Invitrogen) for human cell tracking according to the manufacturer's instructions. hESC-ECs were stained with fluorochrome-conjugated anti-hCD31 and anti-hCD144 antibodies (BD, dilution 1:100) and the PI$^-$ CD31$^+$CD144$^+$ cells were purified on FACS AriaII (BD). A list of antibodies used in flow cytometry is shown in Table 5.

Kidney Capsule Transplantation.

All animal procedures were performed in accordance with protocols approved by University of Oxford or Harvard Medical School. EBs (3-5) or 5 million hESC-derived neural cells were transplanted under the kidney capsule of 12-week-old, female CD-1 mice (Charles River Laboratories International) as described previously[7]. For studying the human gene expression profiles (FIG. 2f), the PI$^-$ DIR$^+$ cells were purified by flow cytometry for subsequent qRT-PCR or microarray analyses.

In Vivo Matrigel Plug Assay and Matrigel Cytometry.

Flow cytometry-purified, 5 million PI$^-$CD31$^+$CD144$^+$ hESC-ECs were resuspended in matrigel and injected subcutaneously into the 12 week-old, female CD-1 mice. Matrigel plugs were harvested at the indicated time points and hESC-ECs were isolated by flow cytometry as described previously[40]. Briefly, matrigel plugs were incubated in PBS supplemented with 25 µg/ml DNase (Sigma), 3 U/ml Dispase and 3 ng/ml Liberase (Roche) for an hour at 37° C. The isolated cells were filtered through a 40 µm nylon mesh (BD) and washed three times with PBS. Isolated cells were then stained with fluorochrome-conjugated anti-hCD31 and anti-hCD144 antibodies; and PI$^-$CD31$^+$CD144$^+$ hESC-ECs were purified from the grafts on FACS AriaII (BD). For studying the human gene expression profiles (FIG. 2F), the PI$^-$CD31$^+$CD144$^+$ cells were also purified by flow cytometry for subsequent qRT-PCR or microarray analyses.

Administration of Therapeutic Antibodies.

Generation of anti-CD4, -CD8 and -CD40L mAbs was described previously[35,41,42]. Non-depleting mAb specific for CD4 (1 mg, clone YTS 177.9) and CD8 (1 mg, clone YTS 105.18) were injected intraperitoneally (i.p.) on days 0, 2 and 4 post transplantation of murine ESC derived EBs. Similarly, non-depleting mAb specific for CD4 (1 mg, clone YTS 177.9), CD8 (1 mg, clone YTS 105.18) and CD40L (1 mg, clone MR1) were injected i.p. on days 0, 2, 4 and 6 after transplantation of hESCs, hiPSCs, hESC-derived neural cells or ECs. In the antigen specificity study, tolerized mice were transplanted with a second graft (Table 3) 3 months after the primary grafts had been transplanted. The 3 months allowed for complete clearance of the therapeutic antibodies as previously described[32,35].

Immunostaining.

Tolerized mice were anaesthetized and perfused intracardially with 4% paraformaldehyde/PBS. Perfused kidney grafts or matrigel plugs were dissected and further fixed in 4% paraformaldehyde at 4° C. for 4 h. The fixed grafts were washed three times with PBS and equilibrated in 30% sucrose before freezing and cryosectioning. Six micrometer sections were blocked in 2% goat serum and then stained with different primary antibodies in 10 µg ml$^{-1}$ at 4° C. overnight. A list of primary antibodies used is shown in Table 4. Alexa-Fluor-488- or Alexa-Fluor-594-conjugated secondary antibodies (Molecular Probes) were also used for unconjugated primary antibodies at room temperature for 30 min in the dark. Slides were mounted with DAPI (4',6-diamidino-2-phenylindole)-containing fluorescence mounting medium (Dako) and fluorescence was detected with a fluorescence microscope (Zeiss). Sections of each lineage were also stained with hematoxylin and eosin for histological analyses. A list of antibodies used in immunostaining is shown in Table 5.

RNA Isolation and Gene Expression Analyses.

Total RNA was isolated from purified cells of both the untreated and mAb-treated groups using the RNeasy mini kit (Qiagen) and reverse transcribed using Superscript III RT (Invitrogen), according to the manufacturer's instructions. Real-time quantitative PCR profiling was analysed on Mastercycler realplex 4 Sequence Detector (Eppendoff) via SYBR Green (Quantitect™ SYBR Green PCR Kit, Qiagen). The relative gene expression level of each sample was expressed as a relative quantitation value determined by the $2^{-ddCT}$ method, which represents the fold change in gene expression normalized to that of a housekeeping gene, Gapdh. The relative gene expression level of each sample was also compared with internal controls as indicated where appropriate. A list of complementary PCR primer sequences used is shown in Table 6.

Microarrays and Functional Annotation.

Total RNA was isolated from purified CD3$^+$ cells of both the untreated and mAb-treated groups using the RNeasy mini kit (Qiagen). RNA was then hybridized to the Affymetrix Mouse 430_2 chips and expression data were analysed with the GeneSpring GX 10.0 software according to the manufacturer's instructions. The normalized data (relative to housekeeping genes) were further analysed for functional annotation using GSEA as described previousl[43,44]. GSEA examines whether a defined set of genes or 'gene sets' are significantly enriched at the top or bottom of a ranked list of genes from microarray experiments, which represent two phenotypes: rejecting control samples and antibody-treated samples. Gene sets including KEGG, Reactome and Biocarta symbols and the GSEA default settings were employed in this study. The microarray data have been deposited in the NCBI Gene Expression Omnibus with an accession number GSE61867.

Statistical Analyses.

The data were expressed as arithmetic means±s.d. of biological triplicate determinations performed under the same conditions. Statistical analysis was performed using the Student's t-test (*$P<0.05$, $P<0.01$ and *$P<0.001$).

TABLE 1

Acceptance rate of fully allogeneic or xenogeneic grafts following coreceptor and costimulation blockade. Mouse EBs derived from CBA/Ca mice ($H-2^k$) or human xenogeneic EBs were transplanted under the kidney capsule of C57B1/6 ($H-2^b$) or outbred CD-1 mice, respectively. Graft acceptance was induced using a short course of coreceptor and costimulation blockade. Transplantation of human EB grafts with or without anti-CD4, -CD8 and -CD40L treatment has been performed over 6 separate experiments with groups of 5 animals in each experiment, respectively.

| Treatments | % graft survival of fully allogeneic murine EB grafts at day 30 post transplantation | % graft survival of xenogeneic human EB grafts at day 30 post transplantation |
|---|---|---|
| No treatment | 0* (n = 5) | 0 (n = 30) |
| aCD4 | 20 (n = 5) | 0 (n = 5) |
| aCD8 | 0 (n = 5) | 0 (n = 5) |
| aCD4 + aCD8 | 100 (n = 10) | 0 (n = 10) |
| aCD4 + aCD8 + aCD40L | not determined | 100 (n = 30) |

*A zero percentage indicates all recipients had rejected the grafts and no graft elements remained at the endpoint of experiments.

TABLE 2

Acceptance rate of human ESC- or iPSC-derived tissues at day 30 or 90 post transplantation following coreceptor and costimulation blockade. Transplantation of human ESC-derived EB grafts or human neural progenitor cells, assessed at the day 30 time-point has been performed over 6 separate experiments with groups of 5 outbred CD-1 mice in each experiment. Transplantation of human iPSC-derived EB grafts or human endothelial cells, assessed at the day 30 time-point has been performed over 2 separate experiments with groups of 5 CD-1 mice, respectively. Transplantation of all types of tissues listed below, assessed at the day 90 time-point has been performed in 2 separate experiments with groups of 5 CD-1 mice, respectively.

| Types of tissues | % graft survival at day 30 post transplantation | % graft survival at day 90 post transplantation |
|---|---|---|
| hESC-derived EBs | 100 (n = 30) | 100 (n = 10) |
| hiPSC-derived EBs | 100 (n = 10) | 100 (n = 10) |
| hESC-derived ectodermal cells (e.g. neural progenitor cells) | 100 (n = 30) | 100 (n = 10) |
| hESC-derived mesodermal cells (e.g. endothelial cells) | 100 (n = 10) | 100 (n = 10) |

TABLE 3

Acceptance of human ESC-derived tissues is tissue antigen-specific and maintained through "linked-suppression". Transplantation experiments listed below have been performed in 6 CD-1 mice for each group.

| Primary graft tolerized for 90 days post transplantation under the kidney capsule | Second graft transplanted s.c. 90 days post transplantation of the primary graft | % survival of the second graft at day 30 post transplantation |
|---|---|---|
| H9 hESC-derived neural progenitors | H9 hESC-derived neural progenitors | 100 (n = 6) |
| H9 hESC-derived neural progenitors | H9 hESC-derived endothelial cells | 100 (n = 6) |
| H9 hESC-derived neural progenitors | H9 hESC-derived EBs | 0* (n = 6) |
| H9 hESC-derived neural progenitors | H1 hESC-derived neural progenitors | 0 (n = 6) |

*A zero percentage indicates all recipients had rejected the grafts and no graft elements remained at the endpoint of experiments.

TABLE 4

Pathway/gene set enrichment analysis (GSEA) showing upregulated (S1A) and downregulated (S1B) genes by tolerized $CD3^+$ T cells.

4A: Pathway analyses of upregulated genes in monoclonal antibodies-treated group compared to the untreated group

| Pathway | p-value | Molecules |
|---|---|---|
| 4-1BB-dependent immune response pathway (BIOCARTA) | 0 | ATF2, MAPKB, MAP4K5, RELA, NFKBIA, JUN, TRAF2, MAP3K1, MAPK14, IKBKB |
| AT1R pathway (BIOCARTA) | 0.019 | ATF2, MEF2D, MAPKB, CALM2, MEF2A, SHC1, PAK1, JUN, PTK2B, GNA0, RAC1, CALM1, PRKCA, SRC, MAP3K1, MAPK3, MEF2C |
| GSK3 pathway (BIOCARTA) | 0.022 | LBP, G5K3B, CCND1, PDPK1, AXIN1, RELA, DVL1, PIK3CA, PPP2CA, CTNNB1, TLR4, APC, TIRAP, CD14, AKT1, PIK3R1, WNT1, LY96, EIF2AK2, GNAT1 |
| Mitochondria pathway (BIOCARTA) | 0.02 | CASP3, BCL2, BTRC3, BTK, DTARLO, CASP7, CASP8 |
| Drug metabolism cytochrome P450 (KEGG) | 0 | FMO2, MGST3, GSTO2, GSTM1, GSTK1, GSTT1, ADH5, MGST1, GSTM2, ADH4, LIGT2A1, GSTM5, GSTA3, GSTO1, CYP2E1, FMO1, CYP1A2, FMO5 |
| Metabolism of xenobiotics by cytochrome P450 (KEGG) | 0 | MGST3, GSTO2, GSTM1, GSTK1, GSTT1, ADH5, MGST1, GSTM2, ADH4, UGT2A1, GSTA3, GSTO1 |
| Intestinal immune network for IgA production (KEGG) | 0.047 | ITGA4, CD86, CD40, TNFSF13B, CXCR4, PTGR, TNFRSF17, TGFB1, IL10 |
| N glycan biosynthesis (KEGG) | 0 | ALG2, ALG12, STT3A, MGAT3, MAN2A2, B4GALT1, MGAT1, ALG14, MAN2A1, MGAT2, B4GALT2, DAD1, MAN1A2, DPM1, DPM2, DPAGT1, ALG5, ALG9, GANAB, MGAT5B |
| HDAC class-III pathway (PID) | 0 | ACS51, MEF2D, SIRT7, CDKN1A, MYOD1, EP300, PPARGC1A, TUBB2A, SIRT2, CREBBP, ACSS2, XRCC6, HDAC4 |
| Destabilization of mRNA by tristetraprolin TTP (REACTOME) | 0 | EXOSC4, EXOSC7, XRN1, EXOSC2, EXOSC9, DCP1A, DCP2 |

TABLE 4-continued

Pathway/gene set enrichment analysis (GSEA) showing upregulated (S1A) and downregulated (S1B) genes by tolerized CD3[+] T cells.

| | | |
|---|---|---|
| Destabilization of mRNA by KSRP (REACTOME) | 0.031 | EXOSC4, YWHAZ, EXOSC7, MAPK11, EXOSC2, EXOSC9, DCP2, MAPK14 |
| Destabilization of mRNA by BRF1 (REACTOME) | 0 | EXOSC4, EXOSC7, XRN1, EXOSC2, EXOSC9, ZFP36L1, DCP1A, DCP2, YWHAB |
| Activation of genes by ATF4 (REACTOME) | 0 | EXOSC4, NFYA, EXOSC7, EXOSC2, EXOSC9, HERPUD1, NFYB, CCL2, ATF6, DDIT3, DCP2 |
| CD28-dependent PI3K/AKT signaling (REACTOME) | 0 | FYN, PIK3R3, CD86, PDPK1, MAP3KR, PIK3CA, PIK3R2, RICTOR, TRIB3, PIK3R1 |
| Adherens junctions interactions (REACTOME) | 0 | CDH1, JUP, PVR, CTNNR1, CDH1A, CDH13, CDH10, CTNNA1, CDH8, CDH5, CDH6, CDH3, CDH15, CDH11, PVRL2, CDH24 |
| Resolution of AP sites via the multiple nucleotide patch replacement pathway (REACTOME) | 0.05 | MPG, TDG, NTHL1, MUTYH |

4B: Pathway analyses of downregulated genes in monoclonal antibodies-treated group compared to the untreated group

| Pathway | p-value | Molecules |
|---|---|---|
| 4-1BB-dependent immune response pathway (BIOCARTA) | 0 | MAP3K5, IL2, CHUK, IFNG, NFKB1, IL4 |
| AT1R pathway (BIOCARTA) | 0.019 | AGT, GRB2, RAF1, ELK1, MAP2K1, PTK2, MAPK1, SOS1, CALM1, EGFR, MAP2K4, MAP2K2 |
| GSK3 pathway (BIOCARTA) | 0.022 | GJA1, FZD1, LEF1, MYD88, IRAK1, NFKB1, TOLLIP |
| Mitochondria pathway (BIOCARTA) | 0.02 | CYCS, BCL2L1, DFFA, DFFB, BAK1, ENDOG, CASP9, APAF1, BAX, BID, BTRC2, CASP6 |
| Drug metabolism cytochrome P450 (KEGG) | 0 | MGST2, GSTP1, ALDH1A3, GSTT2, FMO4, ALDH3A1, MAOA, ALDH3B1, ALDH3B2, GSTM4, MAOB, GSTA4, FMO3, GSTA1, ADH7, GSTA2, UGT2A3, AOX1 |
| Metabolism of xenobiotics by cytochrome P450 (KEGG) | 0 | MGST2, GSTP1, ALDH1A3, GSTT2, ALDH3B1, CYP251, ALDH3B2, CYP251, CYP1A1, GSTM4, GSTA4, GSTA1, ADH7, GSTA2, UGTZA3 |
| Intestinal immune network for IgA production (KEGG) | 0.047 | CCL25, IL2, IL15, CXCL12, LTBR, ICOS, CD80, ITGB7, AICDA, CCR10, TNFRSF13B, IL4, TNFRSF13C, CCL28, MADCAM1, CCR9 |
| N glycan biosynthesis (KEGG) | 0 | ST6GAL1, ALG6, MAN1B1, ALG10B, DPM3, RPN2, ALG8, ALG11 |
| Destabilization of mRNA by tristetraprolin TTP (REACTOME) | 0 | TNPO1 |
| Destabilization of mRNA by KSRP (REACTOME) | 0.031 | PARN, EXOSC5 |
| Destabilization of mRNA by BRF1 (REACTOME) | 0 | MAPKAPK2, EXOSC5 |
| Activation of genes by ATF4 (REACTOME) | 0 | EXOSC5, ATF3 |
| CD28-dependent PI3K/AKT signaling (REACTOME) | 0 | CD80 |
| Adherens junctions interactions (REACTOME) | 0 | CDH7, PVRL4, CDH9, CDH2 |
| Resolution of AP sites via the multiple nucleotide patch replacement pathway (REACTOME) | 0.05 | POLD3, PCNA, APEX1, SMUG1, POLD4, LIG1, OGG1 |

In the GESA report, a p value of zero (0.0) indicates an actual p value of less than 1/number-of-permutations. 1000 permutations were performed hence a value of 0 is equivalent to $p < 0.0001$.

TABLE 5

A list of primary antibodies used in this study:

| Antibody | Company |
|---|---|
| CD3 (marker for T-cells) | eBiosciences |
| CD4 (marker for helper T-cells) | eBiosciences |
| CD8 (marker for cytotoxic T-cells) | eBiosciences |
| CD25 (marker for activated T-cells) | eBiosciences |
| CD31 (marker for endothelial cells) | eBiosciences |
| CD144 (marker for endothelial cells) | Abcam |
| DiR (DiIC$_{18}$(7)) (cell-tracking dye) | Life technologies |
| eNOS (marker for endothelial cell-specific nitric oxide synthase) | Abcam |
| FoxP3 (marker for regulatory T-cells) | eBiosciences |
| Isotype controls | eBiosciences |
| N-Cadherin (marker for neural cells) | Abcam |
| Nestin (marker for neural cells) | Abcam |
| Neurofilament (marker for neural cells) | Abcam |
| Tra-1-60 (marker for pluripotent cells) | eBiosciences |
| vWF (marker for endothelial cells) | Abcam |

A List of Antibodies for Immunostaining or Flow Cytometry Used in this Study:

| Antibody | Clone | Function | Company |
|---|---|---|---|
| CD3-FITC | HIT3a | marker tor T-cells | Biolegend |
| CD4-FITC | RM4-5 | marker for helper T-cells | eBiosciences |
| CD8-Biotin | 53-6.7 | marker for cytotoxic T-cells | eBiosciences |
| CD25-PE | PC61.5 | marker for activated T-cells | eBiosciences |
| CD31-Biotin | WM59 | marker for endothelial cells | eBiosciences |
| CD144-APC | 16B1 | marker for endothelial cells | Abcam |
| DiR (DiIC$_{18}$(7)) | N/A | cell-tracking dye | Life technologies |
| eNOS (unconjugated) | N/A | marker for endothelial cell-specific nitric oxide synthase | Abcam |
| FoxP3-APC | FJK-16s | marker for regulatory T-cells | eBiosciences |
| N-Cadherin (unconjugated) | N/A | marker for neural cells | Abcam |
| Nestin (unconjugated) | 2C1.3A11 | marker for neural cells | Abcam |
| Neurofilament (unconjugated) | N/A | marker for neural cells | Abcam |
| Tra-1-60-PE | Tra-1-60 | marker for pluripotent cells | eBiosciences |
| vWF (unconjugated) | N/A | marker for endothelial cells | Abcam |

TABLE 6

A list of qPCR primer sequences.

Human Genes Forward (SEQ ID NOS: 1-21) Reverse (SEQ ID NOS: 22-42)

| Gene | Forward | Reverse |
|---|---|---|
| Cd31 | AACAGTGTTGACATGAAGAGCC | TGTAAAACAGCACGTCATCCTT |
| eNos | TGATGGCGAAGCGAGTGAAG | ACTCATCCATACACAGGACCC |
| e-selectin | AGAGTGGAGCCTGGTCTTACA | CCTTTGCTGACAATAAGCACTGG |
| Gapdh | GGAGCGAGATCCCTCCAAAAT | GGCTGTTGTCATACTTCTCATGG |
| Gfap | CTGCGGCTCGATCAACTCA | TCCAGCGACTCAATCTTCCTC |
| Icam1 | ATGCCCAGACATCTGTGTCC | GGGGTCTCTATGCCCAACAA |
| Id1 | CTGCTCTACGACATGAACGG | GAAGGTCCCTGATGTAGTCGAT |
| Isl1 | GCGGAGTGTAATCAGTATTTGGA | GCATTTGATCCCGTACAACCT |
| Kdr | GGCCCAATAATCAGAGTGGCA | CCAGTGTCATTTCCGATCACTTT |
| Mbp | GTCCCTGAGCAGATTTAGCTG | GAATCCCTTGTGAGCCGATTT |
| NCad | TCAGGCGTCTGTAGAGGCTT | ATGCACATCCTTCGATAAGACTG |
| Nestin | CTGCTACCCTTGAGACACCTG | GGGCTCTGATCTCTGCATCTAC |
| NeuN | CCAAGCGGCTACACGTCTC | CGTCCCATTCAGCTTCTCCC |
| Neurod1 | ATGACCAAATCGTACAGCGAG | GTTCATGGCTTCGAGGTCGT |
| Olig1 | TACTATGCGGTTTCCCAGGC | GCTGAGTAGGGCAGGATGA |
| Olig2 | CCAGAGCCCGATGACCTTTTT | CACTGCCTCCTAGCTTGTCC |
| p-selectin | ACTGCCAGAATCGCTACACAG | CACCCATGTCCATGTCTTATTGT |
| S100b | TGGCCCTCATCGACGTTTTC | ATGTTCAAAGAACTCGTGGCA |
| Tie2 | TTAGCCAGCTTAGTTCTCTGTGG | AGCATCAGATACAAGAGGTAGGG |
| Vcam1 | GGGAAGATGGTCGTGATCCTT | TCTGGGGTGGTCTCGATTTTA |
| vwf | CCGATGCAGCCTTTTCGGA | TCCCCAAGATACACGGAGAGG |

Mouse Genes Forward (SEQ ID NOS: 43-47 Reverse (SEQ ID NOS: 58-72)

| Gene | Forward | Reverse |
|---|---|---|
| Gapdh | AGGTCGGTGTGAACGGATTTG | TGTAGACCATGTAGTTGAGGTCA |
| Ifnb | ATGACCAACAAGTGTCTCCTCC | GGAATCCAAGCAAGTTGTAGCTC |
| Ifng | ATGAACGCTACACACTGCATC | CCATCCTTTTGCCAGTTCCTC |
| Il 1b | GCAACTGTTCCTGAACTCAACT | ATCTTTTGGGGTCCGTCAACT |
| Il2 | TGAGCAGGATGGAGAATTACAGG | GTCCAAGTTCATCTTCTAGGCAC |
| Il4 | GGTCTCAACCCCCAGCTAGT | GCCGATGATCTCTCTCAAGTGAT |
| Il6 | TAGTCCTTCCTACCCCAATTTCC | TTGGTCCTTAGCCACTCCTTC |
| Il 10 | GCTCTTACTGACTGGCATGAG | CGCAGCTCTAGGAGCATGTG |
| Il 12b | TGGTTTGCCATCGTTTTGCTG | ACAGGTGAGGTTCACTGTTTCT |
| Il 17a | TTTAACTCCCTTGGCGCAAAA | CTTTCCCTCCGCATTGACAC |
| Il23a | ATGCTGGATTGCAGAGCAGTA | ACGGGGCACATTATTTTTAGTCT |
| Tgfb1 | GGCCAGATCCTGTCCAAGC | GTGGGTTTCCACCATTAGCAC |
| Tgfb2 | CTTCGACGTGACAGACGCT | GCAGGGGCAGTGTAAACTTATT |
| Tgfb3 | CCTGGCCCTGCTGAACTTG | TTGATGTGGCCGAAGTCCAAC |
| Tnfa | CCTCTCTCTAATCAGCCCTCTG | GAGGACCTGGGAGTAGATGAG |

All patents, patent applications, and other publications, including GenBank Accession Numbers, cited in this application are incorporated by reference in the entirety for all purposes.

REFERENCES

1. Takebe, T. et al. Vascularized and functional human liver from an iPSC-derived organ bud transplant. *Nature* 499, 481-484 (2013).
2. Araki, R. et al. Negligible immunogenicity of terminally differentiated cells derived from induced pluripotent or embryonic stem cells. *Nature* 494, 100-104 (2013).
3. Zhao, T., Zhang, Z. N., Rong, Z. & Xu, Y. Immunogenicity of induced pluripotent stem cells. *Nature* 474, 212-215 (2011).
4. Lebkowski, J. GRNOPC1: the world's first embryonic stem cell-derived therapy. Interview with Jane Lebkowski. *Regen. Med.* 6, 11-13 (2011).
5. Schwartz, S. D. et al. Embryonic stem cell trials for macular degeneration: a preliminary report. *Lancet* 379, 713-720 (2012).
6. Lomax, G. P., Hall, Z. W. & Lo, B. Responsible oversight of human stem cell research: the California Institute for Regenerative Medicine's medical and ethical standards. *PLoS Med.* 4, e114 (2007).
7. Lui, K. O., Boyd, A. S., Cobbold, S. P., Waldmann, H. & Fairchild, P. J. A role for regulatory T cells in acceptance of ESC-derived tissues transplanted across an major histocompatibility complex barrier. *Stem Cells* 28, 1905-1914 (2010).
8. Robertson, N. J. et al. Embryonic stem cell-derived tissues are immunogenic but their inherent immune privilege promotes the induction of tolerance. *Proc. Natl Acad. Sci. USA* 104, 20920-20925 (2007).
9. Waldmann, H., Hilbrands, R., Howie, D. & Cobbold, S. Harnessing FOXP3þ regulatory T cells for transplantation tolerance. *J. Clin. Invest.* 124, 1439-1445 (2014).
10. Preynat-Seauve, O. et al. Neural progenitors derived from human embryonic stem cells are targeted by allogeneic T and natural killer cells. *J. Cell. Mol. Med.* 13, 3556-3569 (2009).
11. Cobbold, S. P. et al. Infectious tolerance via the consumption of essential amino acids and mTOR signaling. *Proc. Natl Acad. Sci. USA* 106, 12055-12060 (2009).
12. Davies, J. D., Leong, L. Y., Mellor, A., Cobbold, S. P. & Waldmann, H. T cell suppression in transplantation tolerance through linked recognition. *J. Immunol.* 156, 3602-3607 (1996).
13. Kendal, A. R. et al. Sustained suppression by Foxp3þ regulatory T cells is vital for infectious transplantation tolerance. *J. Exp. Med.* 208, 2043-2053 (2011).
14. Qin, S. et al. "Infectious" transplantation tolerance. *Science* 259, 974-977 (1993).
15. Pearl, J. I. et al. Short-term immunosuppression promotes engraftment of embryonic and induced pluripotent stem cells. *Cell Stem Cell* 8, 309-317 (2011).

16. Ljung, K. et al. Costimulation blockade induces foxp3(þ) regulatory T cells to human embryonic stem cells. *Biores. Open Access* 2, 455-458 (2013).
17. Honey, K., Cobbold, S. P. & Waldmann, H. CD40 ligand blockade induces CD4þ T cell tolerance and linked suppression. *J. Immunol.* 163, 4805-4810 (1999).
18. Cho, E. G. et al. MEF2C enhances dopaminergic neuron differentiation of human embryonic stem cells in a parkinsonian rat model. *PLoS ONE* 6, e24027 (2011).
19. Lui, K. O. et al. Driving vascular endothelial cell fate of human multipotent Is11þ heart progenitors with VEGF modified mRNA. *Cell Res.* 23, 1172-1186 (2013).
20. Graca, L., Cobbold, S. P. & Waldmann, H. Identification of regulatory T cells in tolerated allografts. *J. Exp. Med.* 195, 1641-1646 (2002).
21. Cobbold, S. P. et al. Induction of foxP3þ regulatory T cells in the periphery of T cell receptor transgenic mice tolerized to transplants. *J. Immunol.* 172, 6003-6010 (2004).
22. Safford, M. et al. Egr-2 and Egr-3 are negative regulators of T cell activation. *Nat. Immunol.* 6, 472-480 (2005).
23. Arpaia, N. et al. Metabolites produced by commensal bacteria promote peripheral regulatory T-cell generation. *Nature* 504, 451-455 (2013).
24. Burzyn, D. et al. A special population of regulatory T cells potentiates muscle repair. *Cell* 155, 1282-1295 (2013).
25. von Boehmer, H. & Daniel, C. Therapeutic opportunities for manipulating T(Reg) cells in autoimmunity and cancer. *Nat. Rev. Drug Discov.* 12, 51-63 (2013).
26. Lui, K. O., Waldmann, H. & Fairchild, P. J. Embryonic stem cells: overcoming the immunological barriers to cell replacement therapy. *Curr. Stem Cell Res. Ther.* 4, 70-80 (2009).
27. Si-Tayeb, K. et al. Highly efficient generation of human hepatocyte-like cells from induced pluripotent stem cells. *Hepatology* 51, 297-305 (2010).
28. Holderfield, M. T. & Hughes, C. C. Crosstalk between vascular endothelial growth factor, notch, and transforming growth factor-beta in vascular morphogenesis. *Circ. Res.* 102, 637-652 (2008).
29. James, D. et al. Expansion and maintenance of human embryonic stem cell-derived endothelial cells by TGFbeta inhibition is Id1 dependent. *Nat. Biotechnol.* 28, 161-166 (2010).
30. Wise, M. P., Bemelman, F., Cobbold, S. P. & Waldmann, H. Linked suppression of skin graft rejection can operate through indirect recognition. *J. Immunol.* 161, 5813-5816 (1998).
31. Regateiro, F. S. et al. Foxp3 expression is required for the induction of therapeutic tissue tolerance. *J. Immunol.* 189, 3947-3956 (2012).
32. Daley, S. R., Ma, J., Adams, E., Cobbold, S. P. & Waldmann, H. A key role for TGF-beta signaling to T cells in the long-term acceptance of allografts. *J. Immunol.* 179, 3648-3654 (2007).
33. Scully, R., Qin, S., Cobbold, S. & Waldmann, H. Mechanisms in CD4 antibody mediated transplantation tolerance: kinetics of induction, antigen dependency and role of regulatory T cells. *Eur. J. Immunol.* 24, 2383-2392 (1994).
34. Kim, J. M., Rasmussen, J. P. & Rudensky, A. Y. Regulatory T cells prevent catastrophic autoimmunity throughout the lifespan of mice. *Nat. Immunol.* 8, 191-197 (2007).
35. Qin, S. X. et al. Induction of tolerance in peripheral T cells with monoclonal antibodies. *Eur. J. Immunol.* 20, 2737-2745 (1990).
36. Chen, Z., Cobbold, S., Metcalfe, S. & Waldmann, H. Tolerance in the mouse to major histocompatibility complex-mismatched heart allografts, and to rat heart xenografts, using monoclonal antibodies to CD4 and CD8. *Eur. J. Immunol.* 22, 805-810 (1992).
37. Sachs, D. H., Kawai, T. & Sykes, M. Induction of tolerance through mixed chimerism. *Cold Spring Harb. Perspect. Med.* 4, a015529 (2014).
38. Piotti, G., Ma, J., Adams, E., Cobbold, S. & Waldmann, H. Guiding postablative lymphocyte reconstitution as a route toward transplantation tolerance. *Am. J. Transplant.* 14, 1678-1689 (2014).
39. Kirk, A. D. et al. Renal transplantation using belatacept without maintenance steroids or calcineurin inhibitors. *Am. J. Transplant.* 14, 1142-1151 (2014).
40. Adini, A. et al. Matrigel cytometry: a novel method for quantifying angiogenesis in vivo. *J. Immunol. Methods* 342, 78-81 (2009).
41. Noelle, R. J. et al. A 39-kDa protein on activated helper T cells binds CD40 and transduces the signal for cognate activation of B cells. *Proc. Natl Acad. Sci. USA* 89, 6550-6554 (1992).
42. Qin, S. X., Cobbold, S., Benjamin, R. & Waldmann, H. Induction of classical transplantation tolerance in the adult. *J. Exp. Med.* 169, 779-794 (1989).
43. Mootha, V. K. et al. PGC-1alpha-responsive genes involved in oxidative phosphorylation are coordinately downregulated in human diabetes. *Nat. Genet.* 34, 267-273 (2003).
44. Subramanian, A. et al. Gene set enrichment analysis: a knowledge-based approach for interpreting genome-wide expression profiles. *Proc. Natl Acad. Sci. USA* 102, 15545-15550 (2005).
45. Lui, K. O. et al., Tolerance induction to human stem cell transplants with extension to their differentiated progeny. *Nature Communications,* 2014 Dec. 1; 5:5629. doi: 10.1038/ncomms6629.

What is claimed is:

1. A method of inhibiting an immune response against a tissue graft transplanted into a subject, whereby immunological acceptance of the graft in the subject is improved, wherein the method comprises:
   preparing the tissue graft by differentiating and separating cells from a line of pluripotent stem cells (PSCs) into an isolated population of neural progenitor cells;
   transplanting the graft into the subject; and
   administering systemically to the subject an effective combination of an amount of an antibody that is specific for CD4 and an amount of an antibody that is specific for CD8 before, during, and/or after the graft is transplanted into the subject.

2. The method of claim 1, wherein the effective combination further comprises an amount of an antibody specific for CD40L that is administered before, during, and/or after the graft is transplanted into the subject.

3. The method of claim 1, wherein the graft is prepared by differentiating a line of allogeneic embryonic stem cells.

4. The method of claim 1, comprising:
   (a) transplanting into the subject a first tissue graft that has been prepared by differentiating a line of embryonic stem cells;

(b) administering an anybody specific for CD4 and antibody specific for CD8 to the subject periodically following step (a) so as to induce immunological tolerance in the subject to the first allograft; and thereafter (c) transplanting into the subject a second tissue graft that has been prepared by differentiating the same line of embryonic stem cells.

5. The method of claim 4, wherein the second graft has been differentiated from the line of embryonic stem cells into a type of tissue that is different and not derivable from the tissue type of the first graft.

6. The method of claim 2, wherein the antibody specific for CD4, the antibody specific for CD8, and the antibody specific for CD40L are administered to the subject in a plurality of doses within one week following the transplanting of the graft.

7. The method of claim 1, whereby the graft remains viable in the host for at least 3 months.

8. The method of claim 1, wherein the neural progenitor cells are positive for nestin and neurofilament protein.

9. The method of claim 1, wherein the neural progenitor cells are prepared by culturing cells from the PSC line or progeny thereof in a neural differentiation medium containing fibroblast growth factor 2 (FGF2) and epidermal growth factor (EGF).

10. The method of claim 1 wherein the neural progenitor cells are isolated by separating neural rosettes from other PSC derived cells.

11. The method of claim 1, wherein the neural progenitor cells differentiate into neurons, glial cells, and astrocytes following engraftment into the subject.

12. A method of improving acceptance of a graft in a subject in need thereof, comprising:

preparing a tolerizing cell population by differentiating cells from a line of human embryonic stem cells (hESCs) into ectodermal cells of a first tissue type;

transplanting the tolerizing cell population into the subject without irradiating the subject;

administering a plurality of doses of anti-CD4, anti-CD8, and anti-CD40L to the subject concurrently and/or within a week following the transplanting of the first tissue type so as to induce a state of immunological tolerance to the tolerizing cell population and to cells with MHC (major histocompatibility complex) antigens that match the MHC antigens of the tolerizing cell population;

preparing the graft by differentiating cells from the same line of hESCs into a second tissue type that is different and not derivable from the first tissue type; and transplanting the graft into the subject once the state of immunological tolerance has been induced in the subject.

13. The method of claim 12, further comprising monitoring FoxP3 positive T cells in the graft to confirm that the state of immunological tolerance has been induced in the subject.

14. The method of claim 12, whereby the graft remains viable in the host for at least 3 months.

15. The method of claim 1, wherein cells of the graft are allogeneic to the subject being treated.

16. The method of claim 1, wherein cells of the graft are xenogeneic to the subject being treated.

* * * * *